US006613307B1

(12) United States Patent
Cooper

(10) Patent No.: US 6,613,307 B1
(45) Date of Patent: Sep. 2, 2003

(54) AEROSOL FORMULATIONS OF SALMETEROL XINAFOATE

(75) Inventor: Simon Murray Cooper, Bishops Stortford (GB)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/646,872

(22) PCT Filed: Apr. 23, 1999

(86) PCT No.: PCT/EP99/02748

§ 371 (c)(1),
(2), (4) Date: Oct. 5, 2000

(87) PCT Pub. No.: WO99/55319

PCT Pub. Date: Nov. 4, 1999

(30) Foreign Application Priority Data

Apr. 24, 1998 (GB) .............................................. 9808802

(51) Int. Cl.⁷ .............................. A61K 9/14; A61K 9/12
(52) U.S. Cl. .............................. 424/45; 424/46; 424/43; 424/489; 128/200.14; 128/203.12
(58) Field of Search ........................... 424/45, 46, 489; 128/200.14

(56) References Cited

U.S. PATENT DOCUMENTS

| 5,683,676 A | * | 11/1997 | Akehurst et al. .............. 424/45 |
| 5,795,594 A | * | 8/1998 | York et al. .................... 424/489 |
| 5,817,293 A | * | 10/1998 | Akehurst et al. .............. 424/45 |

FOREIGN PATENT DOCUMENTS

| WO | WO 93 11745 A | 6/1993 |
| WO | WO 93 17665 A | 9/1993 |
| WO | WO 95 01324 A | 1/1995 |

* cited by examiner

Primary Examiner—Michael G. Hartley
Assistant Examiner—M. Haghighatian
(74) Attorney, Agent, or Firm—Bacon & Thomas

(57) ABSTRACT

The present invention relates to formulations comprising particulate products which may be prepared by methods and apparatus using supercritical fluids. More particularly, the invention relates to formulations comprising certain crystalline forms of 4-hydroxy-$\alpha^1$-[[[6-(4-phenylbutoxy)hexyl]amino]methyl]-1,3-benzenedimethanol (salmeterol) 1-hydroxy-2-naphthalenecarboxylate (xinafoate). Accordingly, the present invention provides an aerosol pharmaceutical formulation comprising salmeterol xinafoate with a controlled particle size, shape and morphology, and a fluorocarbon, hydrogen-containing fluorocarbon or hydrogen-containing chlorofluorocarbon propellant.

26 Claims, 26 Drawing Sheets

FLOW DIRECTION

θ = ~30°

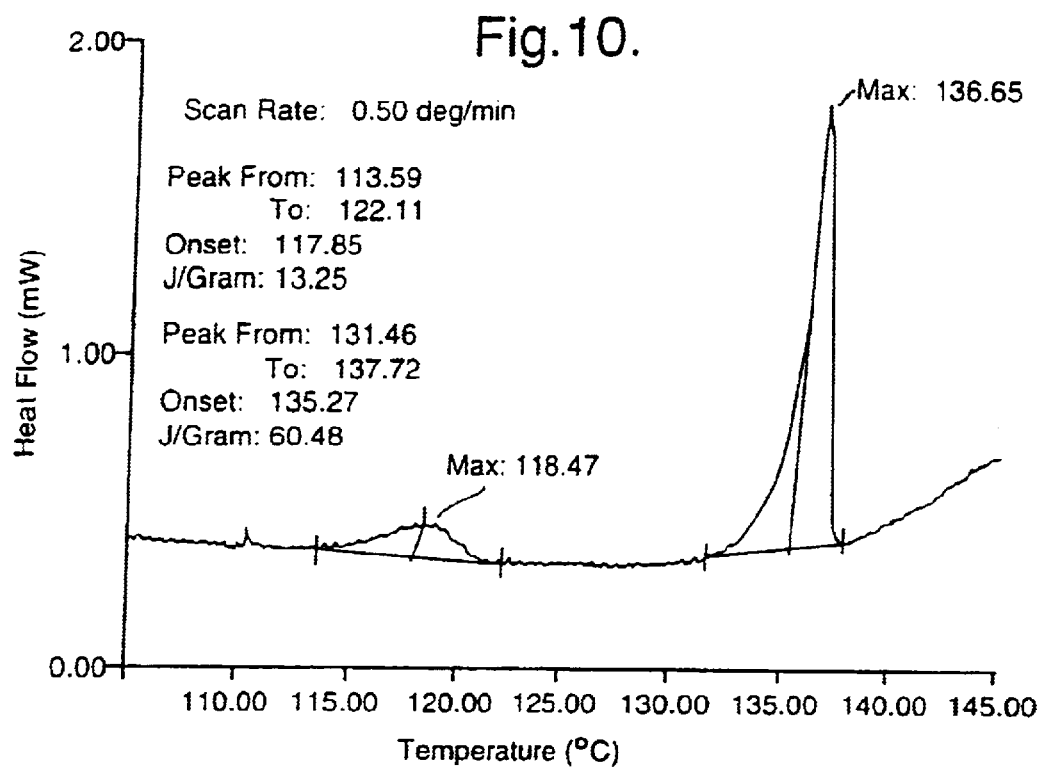
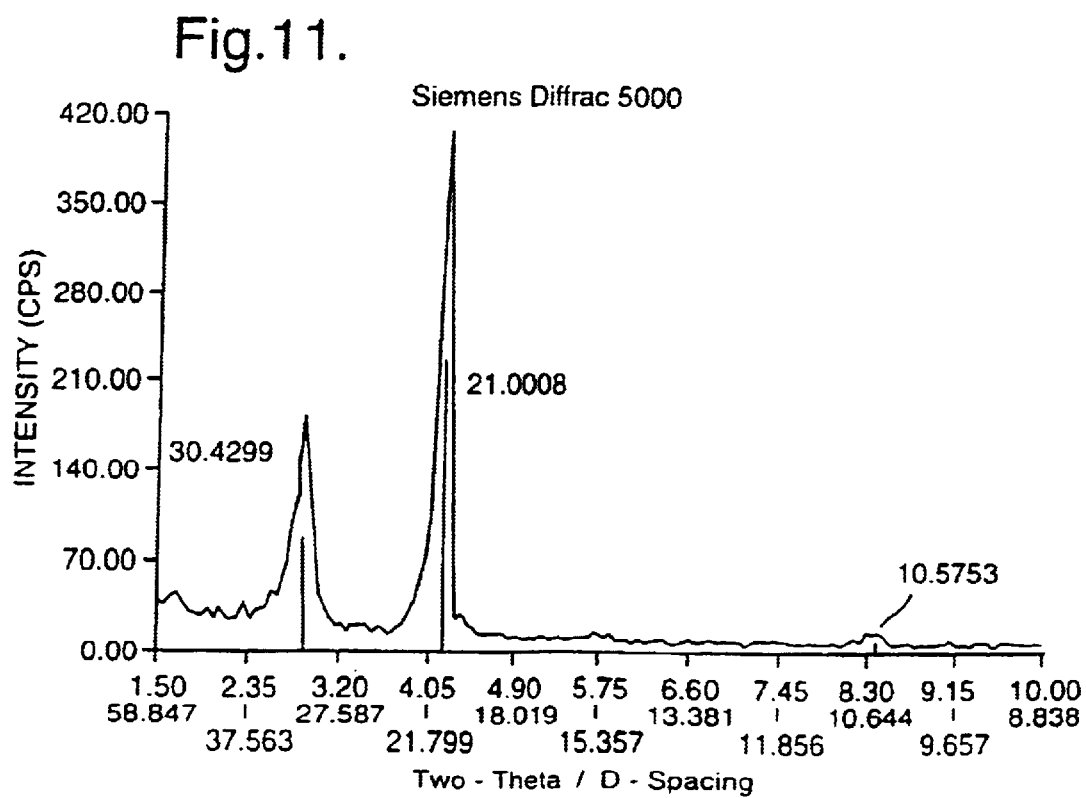

Fig.24.A
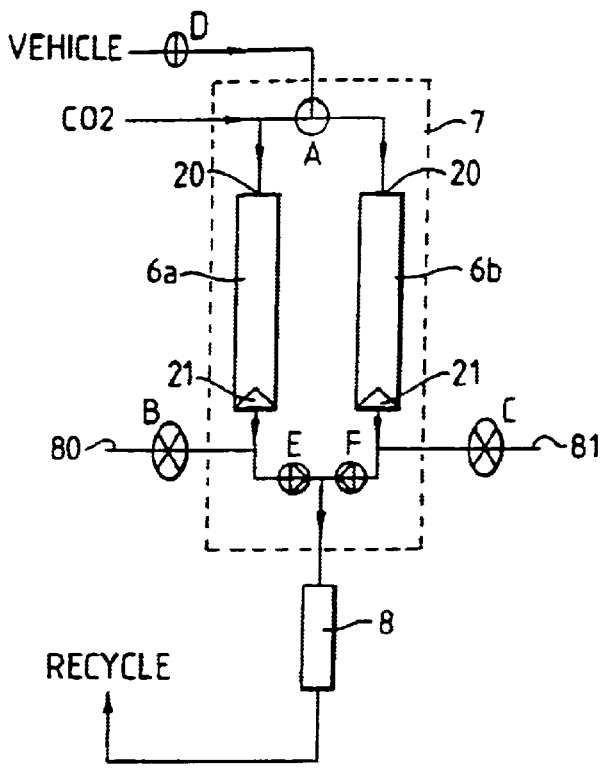
Fig.24.B
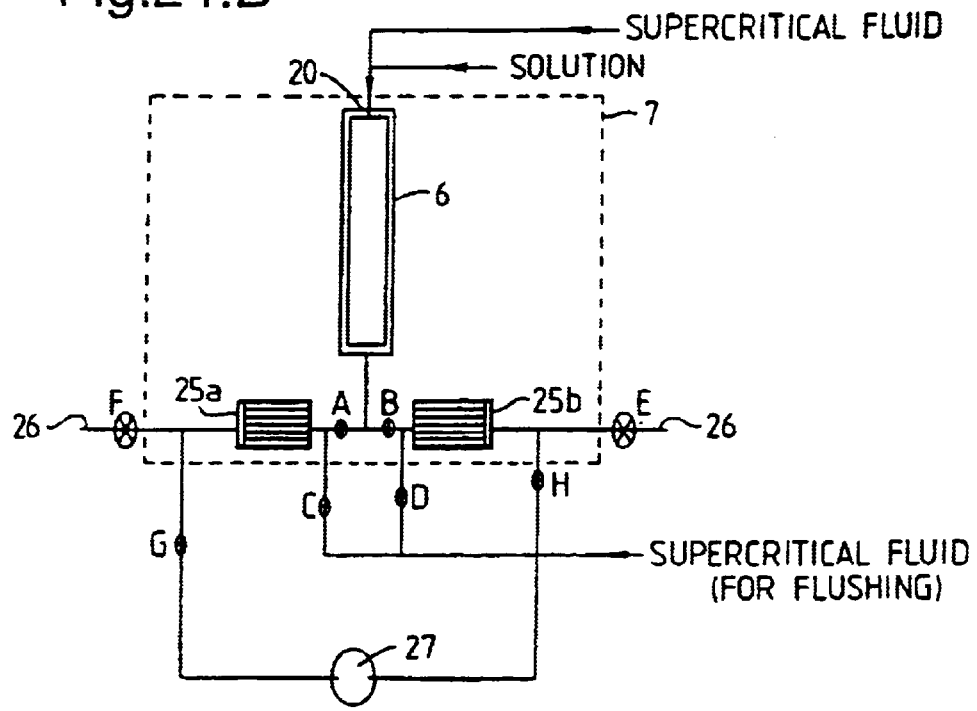

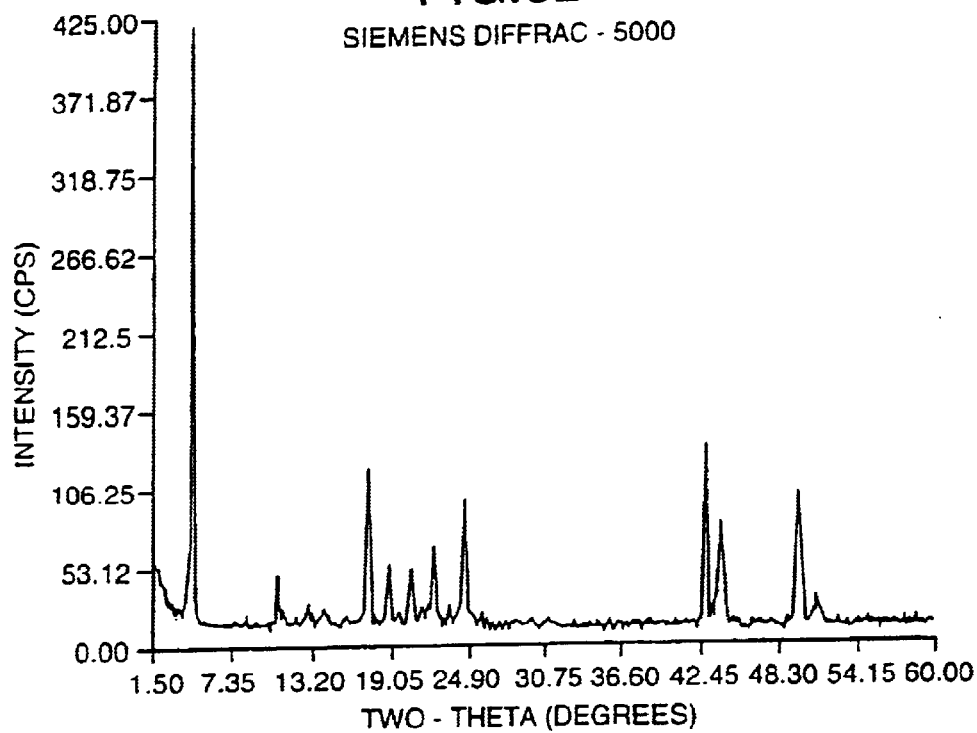
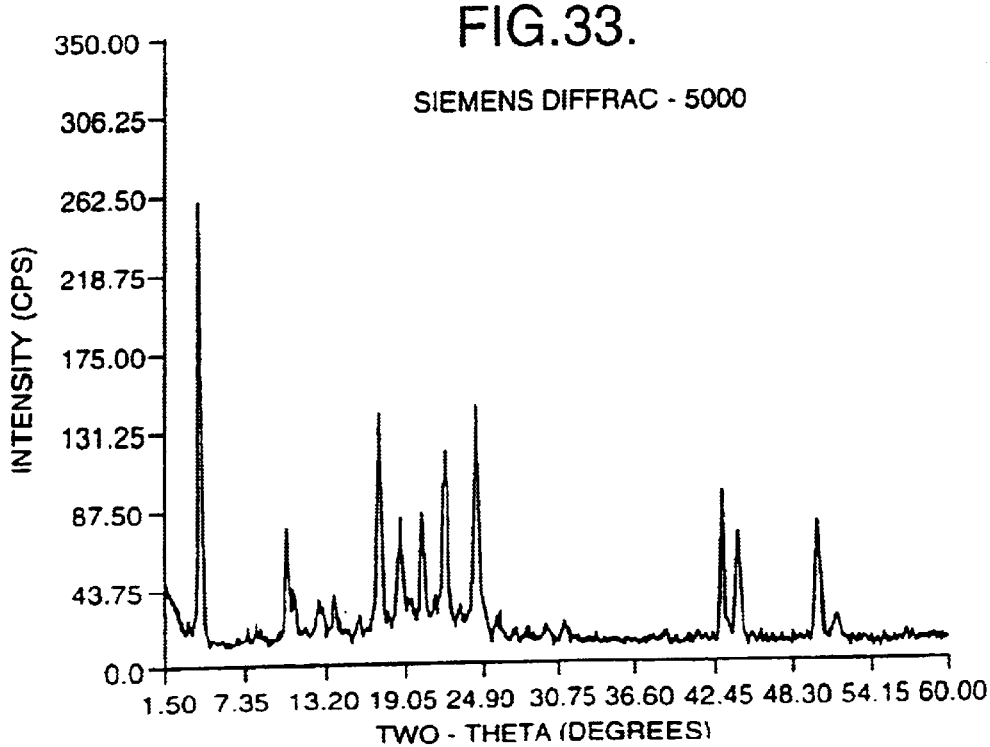

AEROSOL FORMULATIONS OF SALMETEROL XINAFOATE

This application is a 371 of PCT/EP99/02748, filed Apr. 23, 1999.

The present invention relates to formulations comprising particulate products which may be prepared by methods and apparatus using supercritical fluids. More particularly, the invention relates to formulations comprising certain crystalline forms of 4-hydroxy-$\alpha^1$-[[[6-(4-phenylbutoxy)hexyl]amino]methyl]-1,3-benzenedimethanol (salmeterol) 1-hydroxy-2-naphthalenecarboxylate (xinafoate).

Salmeterol is a selective and potent $\beta_2$ adrenoreceptor stimulant bronchodilator which has been very successfully used by inhalation for the immediate relief of spasm in asthma. Salmeterol is described in British Patent Specification No. 2140800. The xinafoate salt of salmeterol is a particularly preferred pharmaceutically acceptable salt for use in inhalation therapy.

The use of aerosols to administer medicaments by inhalation has been known for several decades. Such aerosols generally comprise the medicament, one or more chlorofluorocarbon propellants and either a surfactant or a solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise fluorocarbons hydrogen-containing fluorocarbons and hydrogen-containing chlorofluorocarbons, and a number of medicinal aerosol formulations using such propellant systems are disclosed in, for example, EP 0372777, WO91/04011, WO91/11173. WO91/11495, WO91/14422, WO92/00107, WO93/08447, WO93/08446. WO93/11743, WO93/11744 and WO93/11745. These applications are all concerned with the preparation of pressurised aerosols for the administration of medicaments and seek to overcome the problems associated with the use of the new class of propellants, in particular the problems of stability associated with the pharmaceutical formulations prepared.

Conventionally crystallised salmeterol xinafoate, even after micronisation (fluid milling), exists in a form with poor flow characteristics, for example it is cohesive and statically charged, which results in difficulties in handling the drug substance in pharmaceutical formulation processes and can, when the drug is mixed with fluorocarbon, hydrogen-containing fluorocarbon or hydrogen-containing chlorofluorocarbon propellants, lead to dispersion stability problems such as drug agglomeration or deposition onto components of the aerosol can, valve or actuator.

We have now surprisingly found that it is in fact possible to obtain satisfactory dispersions of salmeterol xinafoate in fluorocarbon, hydrogen-containing fluorocarbon or hydrogen-containing chlorofluorocarbon propellants such as 1,1,1,2-tetrafluoroethane (propellant 134a, or HFA 134a) by use of salmeterol xinafoate with a controlled particle size, shape and morphology.

International patent application PCT/GB94/01425 published under No. WO95/01324 (the disclosure of which is hereby incorporated herein by reference) describes a method and apparatus suitable for the formation of particulate salmeterol xinafoate in a controlled manner utilising a supercritical fluid particle formation system. The apparatus, further details of which are set out below, comprises a particle formation vessel with means for controlling the temperature of said vessel and means for controlling the pressure of said vessel, together with a means for the co-introduction into said vessel of a supercritical fluid and a vehicle containing at least one substance (such as salmeterol xinafoate) in solution or suspension, such that dispersion and extraction of the vehicle occur substantially simultaneously by the action of the supercritical fluid. The simultaneous co-introduction of the vehicle containing at least one substance in solution or suspension and the supercritical fluid, according to the method described in WO95/01324, allows a high degree of control of parameters such as temperature, pressure and flow rate, of both vehicle fluid and supercritical fluid, at the exact point when they come into contact with one another. This gives a high degree of control over the conditions under which particles of the drug substance suspended or dissolved in the vehicle form and thus of the physical properties of the particles formed.

Accordingly, the present invention provides an aerosol pharmaceutical formulation comprising salmeterol xinafoate with a controlled particle size, shape and morphology, and a fluorocarbon, hydrogen-containing fluorocarbon or hydrogen-containing chlorofluorocarbon propellant. Use of such particulate crystalline forms can give particular benefits in relation to reduction of agglomeration and of deposition of drug onto aerosol can walls, actuator and valve components and may permit the formation of stable dispersions without the use of additional components such as surfactants or co-solvents, or with relatively low levels of such components. Adsorption of drug into rubber components of the valve and/or actuator may also be reduced. Minimising and preferably avoiding the use of formulation excipients e.g. surfactants, cosolvents etc. in the aerosol formulations according to the invention may be advantageous since the formulations may be substantially taste and odour free, less irritant and less toxic than conventional formulations. Preferably the propellant is 1,1,1,2-tetrafluoroethane (propellant 134a), in which formulations the weight ratio of drug to propellant is preferably between 0.025:75 and 0.1:75, for example 0.05:75.

Further advantages for particles formed by the supercritical fluid particle formation method and apparatus include control over the quality of the crystalline and polymorphic phases, since the particles will experience the same stable conditions of temperature and pressure when formed, as well as the potential of enhanced purity. This latter feature can be attributed to the high selectivity of supercritical fluids under different working conditions, enabling the extraction of one or more of the impurities from the vehicle containing the substance of interest.

Moreover, the co-introduction of the vehicle and supercritical fluid, leading to simultaneous dispersion and particle formation, allows particle formation to be carried out, if desired, at temperatures at or above the boiling point of the vehicle, something not possible using previous supercritical fluid particle formation techniques. This enables operation in temperature and pressure domains which were previously inaccessible, which in turn can allow the formation of products, or particular forms of products, that previously could not have been achieved.

Control of parameters such as size and shape in the particulate product will be dependent upon the operating conditions used when carrying out the supercritical fluid method. Variables include the flow rates of the supercritical fluid and/or the vehicle containing substance(s), the concentration of the substance(s) in the vehicle, and the temperature and pressure inside the particle formation vessel. Thus the provision of formulations comprising salmeterol xinafoate as prepared by the supercritical fluid (SCF) particle formation method described herein and one or more fluorocarbon, hydrogen-containing fluorocarbon or hydrogen-containing chlorofluorocarbon propellants is a further aspect of the present invention.

In another aspect of the present invention, there is provided an aerosol pharmaceutical formulation comprising salmeterol xinafoate in a form with a dynamic bulk density of less than 0.1 g.cm$^{-3}$, preferably in the range between 0.01 and 0.1 g.cm$^{-3}$ and, in particular, in the range between 0.01 and 0.075 g.cm$^{-3}$ and a fluorocarbon, hydrogen-containing fluorocarbon or hydrogen-containing chlorofluorocarbon propellant.

The dynamic bulk density (W) is indicative of a substance's fluidisability and is defined as:

$$W = \frac{(P-A)C}{100} + A$$

where P is the packed bulk density (g.cm$^{-3}$), A is the aerated bulk density (g.cm$^{-3}$) and C is the compressibility (%) where C is calculated by the equation:

$$C = \frac{P-A}{P} \times 100$$

Clearly, a low figure for W corresponds to a high degree of fluidisability.

When compared against conventionally crystallised salmeterol xinafoate, both before and after micronisation, the salmeterol xinafoate employed in the present invention exhibits a significantly lower dynamic bulk density, as illustrated in Table 2 (see Example 1 below).

It will be appreciated that in the case of an inhaled pharmaceutical, such as salmeterol xinafoate, it is particularly desirable to produce a drug substance which is readily fluidisable, thereby potentially improving its inhalation properties.

The salmeterol xinafoate used in the formulations of the present invention is observed to have improved handling and fluidising characteristics compared with conventionally crystallised salmeterol xinafoate.

Furthermore, the particle size and shape of the salmeterol xinafoate used in the formulations of the present invention can be controlled as illustrated by the electron-micrographs herein.

Preferably, the salmeterol xinafoate employed in the formulations of the present invention is within the particle size range suitable for pharmaceutical dosage forms to be delivered by inhalation or insufflation. A suitable particle size range for this use is 1 to 10 microns, preferably 1 to 5 microns. Particles generally have a uniform particle size distribution, as measured by a uniformity coefficient of from 1 to 100, typically 1 to 20 e.g. 5 to 20.

The salmeterol xinafoate employed in the formulations of the present invention typically has a low cohesivity, for example of 0 to 20%, preferably 0 to 5% employing methods of measurement based on those described by R L Carr in Chemical Engineering 1965, 163–168.

It has also been found that conventionally crystallised salmeterol xinafoate, when studied by differential scanning calorimetry (DSC), shows a transition between two forms (hereinafter "Polymorph I" and "Polymorph II") occurring between 120° C. and 140° C. A DSC profile for conventionally crystallised salmeterol xinafoate showing the characteristic two peaks for Polymorphs I and II is shown in FIG. 3. However, use of the supercritical fluid particle formation method and apparatus of WO95/01324 allows the preparation of substantially pure Polymorph I, substantially pure Polymorph II or controlled mixtures of the two polymorphic forms. The prepared polymorphs are also stable, meaning that there is no transition from one polymorph to another observed under the DSC conditions.

Thus, the present invention also provides a pharmaceutical aerosol formulation which comprises substantially pure particulate Polymorph I salmeterol xinafoate and a fluorocarbon, hydrogen-containing fluorocarbon or hydrogen-containing chlorofluorocarbon propellant. Also provided is a pharmaceutical aerosol formulation which comprises substantially pure particulate Polymorph II salmeterol xinafoate and a fluorocarbon, hydrogen-containing fluorocarbon or hydrogen-containing chlorofluorocarbon propellant. By "substantially pure" polymorph is meant a composition containing a first polymorph, but essentially none of the other polymorph; by "essentially none" is meant less than 0.5% w/w based upon the first polymorph, for example 0.1% or less.

The present invention also provides the use of essentially pure Polymorph I of salmeterol xinafoate in the manufacture of a medicament comprising propellant 134a for the treatment of respiratory disorders.

The salmeterol xinafoate prepared by the supercritical fluid particle formation method may be used to prepare a pharmaceutical composition which further comprises a pharmaceutically acceptable carrier. Preferred carriers include, for example polymers e.g. starch and hydroxypropylcellulose, silicon dioxide, sorbitol, mannitol and lactose e.g. lactose monohydrate. Using the supercritical fluid particle formation method and apparatus, salmeterol xinafoate and a carrier may be co-crystallised together to form multicomponent particles comprising both salmeterol xinafoate and carrier. Pharmaceutical formulations comprising such multicomponent particles and a fluorocarbon, hydrogen-containing fluorocarbon or hydrogen-containing chlorofluorocarbon propellant represent a further aspect of the invention. In a preferred aspect, the invention provides a pharmaceutical composition comprising salmeterol xinafoate and lactose in the form of multicomponent particles.

The use of supercritical fluids (SCFs) and the properties thereof has been extensively documented, see for instance, J. W. Tom and P. G. Debendetti, "Particle Formation with Supercritical Fluids—A Review", *J. Aerosol. Sci.*, 22 (5), 555–584 (1991). Briefly, a supercritical fluid can be defined as a fluid at or above its critical pressure ($P_c$) and critical temperature ($T_c$) simultaneously. Supercritical fluids have been of considerable interest, not least because of their unique properties. These characteristics include:

High diffusivity, low viscosity and low surface tension compared with liquids.

Large compressibility of supercritical fluids compared with the ideal gas implies large changes in fluid density for slight changes in pressure, which in turn results in highly controllable solvation power. Supercritical fluid densities typically range from 0.1–0.9 g/ml under normal working conditions. Thus, selective extraction with one supercritical fluid is possible.

Many supercritical fluids are normally gases under ambient conditions, which eliminates the evaporation/concentration step needed in conventional liquid extraction.

Most of the commonly used supercritical fluids create non-oxidising or non-degrading atmospheres for sensitive and thermolabile compounds, due to their inertness and moderate temperatures used in routine working conditions. Carbon dioxide is the most extensively used SCF due to its cheapness, non-toxicity, non-flammability and low critical temperature.

These characteristics have led to the development of several techniques of extraction and particle formation utilising supercritical fluids, including that described in WO95/01324.

As used herein, the term "supercritical fluid" means a fluid at or above its critical pressure ($P_c$) and critical temperature ($T_c$) simultaneously. In practice, the pressure of the fluid is likely to be in the range 1.01 $P_c$–7.0 $P_c$, and its temperature in the range 1.01 $T_c$–4.0 $T_c$.

The term "vehicle" means a fluid which dissolves a solid or solids, to form a solution, or which forms a suspension of a solid or solids which do not dissolve or have a low solubility in the fluid. The vehicle can be composed of one or more fluids.

As used herein, the term "supercritical solution" means a supercritical fluid which has extracted and dissolved the vehicle.

The term "dispersion" means the formation of droplets of the vehicle containing at least one substance in solution or suspension.

The term "particulate product" includes products in a single-component or multi-component (e.g. intimate mixtures of one component in a matrix of another) form.

Suitable chemicals for use as supercritical fluids include carbon dioxide, nitrous oxide, sulphur hexafluoride, xenon, ethylene, chlorotrifluoromethane, ethane and trifluoromethane. Particularly preferred is carbon dioxide.

The supercritical fluid may optionally contain one or more modifiers, for example, but not limited to, methanol, ethanol, isopropanol or acetone. When used, the modifier preferably constitutes not more than 20%, and more particularly constitutes between 1 and 10%, of the supercritical fluid.

The term "modifier" is well known to those persons skilled in the art. A modifier (or co-solvent) may be described as a chemical which, when added to a supercritical fluid, changes the intrinsic properties of the supercritical fluid in or around the critical point.

It will be appreciated that the precise conditions of operation of the present apparatus will be dependent upon the choice of supercritical fluid and whether or not modifiers are present. Table 1 lists the critical pressure and temperatures for some selected fluids:

TABLE 1

| Fluid | $P_c$ (bar) | $T_c$ (° C.) |
|---|---|---|
| carbon dioxide | 74 | 31 |
| nitrous oxide | 72 | 36 |
| sulphur hexafluoride | 37 | 45 |
| xenon | 58 | 16 |
| ethylene | 51 | 10 |
| chlorotrifluoromethane | 39 | 29 |
| ethane | 48 | 32 |
| trifluoromethane | 47 | 26 |

In practice, it may be preferable to maintain the pressure inside the particle formation vessel substantially in excess of the $P_c$ (for instance, 100–300 bar for carbon dioxide) whilst the temperature is slightly above the $T_c$ (e.g. 40–60° C. for carbon dioxide).

The flow rates of the supercritical fluid and/or the vehicle may also be controlled so as to achieve a desired particle size, shape and/or form. Typically, the ratio of the vehicle flow rate to the supercritical fluid flow rate will be between 0.001 and 0.1, preferably between 0.01 and 0.07, more preferably around 0.03.

The method described herein preferably additionally involves collecting the particulate product following its formation. It may also involve recovering the supercritical solution formed, separating the components of the solution and recycling one or more of those components for future use.

It will be appreciated that the choice of a suitable combination of supercritical fluid, modifier (where desired) and vehicle will be well within the capabilities of a person of ordinary skill in the art.

In the present case, the product to be formed is a pharmaceutical compound, salmeterol xinafoate, for which a suitable solvent may be, for example, methanol, ethanol, isopropanol, acetone or any mixture thereof.

Control of parameters such as size and shape in the particulate product will be dependent upon the operating conditions used when carrying out the supercritical fluid particle formation method. Variables include the flow rates of the supercritical fluid and/or the vehicle containing the drug, the concentration of the drug in the vehicle, and the temperature and pressure inside the particle formation vessel.

The apparatus described herein and its use provide the opportunity for manufacturing dry particulate products with controlled particle size, shape and morphology by offering such control over the working conditions, especially the pressure, utilising, for example, an automated back-pressure regulator such as model number 880-81 produced by Jasco Inc. Such control can eliminate pressure fluctuation across the particle formation vessel and ensures a more uniform dispersion by the supercritical fluid of the vehicle containing drug substance, with narrow droplet size distribution, during the particle formation process. There is little or no chance that the dispersed droplets will reunite to form larger droplets since the dispersion occurs by the action of the supercritical fluid which also ensures thorough mixing with the vehicle and rapidly removes the vehicle from the drug substance, leading to particle formation.

The means for the co-introduction of the supercritical fluid and the vehicle into the particle formation vessel preferably allows for them to be introduced with concurrent directions of flow, and more preferably takes the form of a coaxial nozzle as described below. This ensures no contact between the formed particles and the vehicle fluid around the nozzle tip area. Such contact would reduce control of the final product size and shape. Extra control over the droplet size, in addition to that provided by nozzle design, is achieved by controlling the flow rates of the supercritical fluid and the vehicle fluid. At the same time, retaining the particles in the particles formation vessel eliminates the potential of contact with the vehicle fluid that might otherwise take place on depressurising the supercritical solution. Such contact would affect the shape and size, and potentially the yield, of the product.

A further advantage of the apparatus described herein is that it can allow particle formation to occur in a completely closed environment, i.e. in a closed particle formation vessel. The apparatus can be sealed from the atmosphere, making it easy to maintain sterile operating conditions and also reducing the risk of environmental pollution and it can also be kept free of oxygen, moisture or other relevant contaminants.

The final aerosol formulation desirably contains 0.03–0.13% w/w, preferably 0.07% w/w, of medicament relative to the total weight of the formulation.

The propellants for use in the invention may be any fluorocarbon, hydrogen-containing fluorocarbon or hydrogen-containing chlorofluorocarbon propellant or mixtures thereof having a sufficient vapour pressure to render them effective as propellants. Preferably the propellant will be a non-solvent for the medicament. Suitable propellants include, for example, $C_{1-4}$hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbon, hydrogen-containing fluorocarbon or hydrogen-containing chlorofluorocarbon propellants are employed they may be mixtures of the above identified compounds or mixtures, preferably binary mixtures, with other fluorocarbon, hydrogen-containing fluorocarbon or hydrogen-containing chlorofluorocarbon propellants for example $CHClF_2$, $CH_2F_2$ and $CF_3CH_3$. Preferably a single fluorocarbon, hydrogen-containing fluorocarbon or hydrogen-containing chlorofluorocarbon is employed as the propellant. Particularly preferred as propellants are $C_{1-4}$hydrogen-containing fluorocarbons such as 1,1,1,2-tetrafluoroethane ($CF_3CH_2F$) and 1,1,1,2,3,3,3-heptafluoro-n-propane ($CF_3CHFCF_3$), particularly 1,1,1,2-tetrafluoroethane.

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

The propellant may additionally contain a volatile adjuvant such as a saturated hydrocarbon for example propane, n-butane, isobutane, pentane and isopentane or a dialkyl ether for example dimethyl ether. In general, up to 50% w/w of the propellant may comprise a volatile hydrocarbon, for example 1 to 30% w/w. However, formulations which are substantially free of volatile adjuvants are preferred.

The benefits of the present invention may be achieved without the use of any surfactant or cosolvent in the composition, or with relatively low levels of such components, and without the necessity to pre-treat the medicament prior to dispersal in the propellant. However, it is further envisaged that certain formulations of the present invention may include liquid components of higher polarity than the propellant employed. Polarity may be determined for example, by the method described in European Patent Application Publication No. 0327777. In particular, where such components are included, alcohols such as ethanol are preferable. However, higher polarity liquid components are preferably included at relatively low concentrations, for example less than 5%, preferably less than 1% w/w based upon the fluorocarbon or hydrogen-containing chlorofluorocarbon. Particular preferred formulations may contain essentially no higher polarity liquid components, by "essentially no" is meant less than 0.1% w/w based upon propellant, for example 0.0001% or less.

Where a surfactant is employed, it is selected from those which are physiologically acceptable upon administration by inhalation such as oleic acid, sorbitan trioleate (Span R 85), sorbitan mono-oleate, sorbitan monolaurate, polyoxyethylene (20) sorbitan monolaurate, polyoxyethylene (20) sorbitan monooleate, natural lecithin, fluorinated and perfluorinated surfactants including fluorinated lecithins, fluorinated phosphatidylcholines, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil and sunflower seed oil.

If it is desired to provide a formulation in which the particulate medicament is pre-coated with surfactant, the use of substantially non-ionic surfactants which have reasonable solubility in substantially non-polar solvents is frequently advantageous since it facilitates coating of the medicament particles using solutions of surfactant in non-polar solvents in which the medicament has limited or minimal solubility. The particulate drug, with its dry coating of surfactant may than be suspended in propellant, optionally with a co-solvent such as ethanol. Such formulations are described in WO92/08446 and WO92/08447.

A particularly preferred embodiment of the invention provides a pharmaceutical aerosol formulation consisting essentially of salmeterol xinafoate, as prepared by the supercritical fluid particle formation process described herein, and a fluorocarbon, hydrogen-containing fluorocarbon or hydrogen-containing chlorofluorocarbon propellant.

It will be appreciated by those skilled in the art that the aerosol formulations according to the invention may, if desired, contain a combination of two or more active ingredients. Aerosol compositions containing two active ingredients (in a conventional propellant system) are known, for example, for the treatment of respiratory disorders such as asthma. Accordingly, the present invention further provides aerosol formulations in accordance with the invention which contain salmeterol xinafoate and one or more additional particulate medicaments. Medicaments may be selected from any other suitable drug useful in inhalation therapy and which may be presented in a form which is substantially completely insoluble in the selected propellant. Appropriate medicaments may thus be selected from, for example, salbutamol, fluticasone propionate or beclomethasone dipropionate; analgesics, e.g. codeine, dihydromorphine, ergotamine, fentanyl or morphine; anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; anti-inflammatories, e.g. flunisolide, budesonide, tipredane or triamcinolone acetonide; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, (–)-4-amino-3,5-dichloro-α-[[[6-[2-(2-pyridinyl)ethoxy]hexyl]amino]methyl]benzenemethanol or orciprenaline; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant.

Particularly preferred aerosol drug combination formulations contain salmeterol as the xinafoate salt in combination with an antiinflammatory steroid such as a beclomethasone ester (e.g. the dipropionate) or a fluticasone ester (e.g. the propionate) or an antiallergic such as cromoglycate (e.g. the sodium salt). Combinations of salmeterol and fluticasone propionate or beclomethasone dipropionate are preferred, especially salmeterol xinafoate and fluticasone propionate. In particularly preferred combined formulations, each particulate drug will be of controlled particle size, shape and morphology such as may be formed by means of supercritical fluid particle formation as described herein.

The formulations of the present invention may be prepared by dispersal of the particulate salmeterol xinafoate (and carrier or additional drug if present) in the selected propellant in an appropriate container, e.g. with the aid of sonication. The process is desirably carried out under anhydrous conditions to obviate any adverse effects of moisture on suspension stability.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The particle size distribution of the aerosol formulations according to the invention may be measured by conventional techniques, for example by cascade impaction or by the "Twin Impinger" analytical process. As used herein reference to the "Twin Impinger" assay means "Determination of the deposition of the emitted dose in pressurised inhalations using apparatus A" as defined in British Pharmacopoeia 1988, pages A204–207, Appendix XVII C. Such techniques enable the "respirable fraction" of the aerosol formulations to be calculated. As used herein reference to "respirable fraction" means the amount of active ingredient collected in the lower impingement chamber per actuation expressed as a percentage of the total amount of active ingredient delivered per actuation using the twin impinger method described above. The formulations according to the invention, containing salmeterol xinafoate of mean particle size between 1 and 10 microns, preferably have a respirable fraction of 30% or more by weight of the medicament, desirably 30 to 70%, for example 30 to 50%.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer-coated and/or plastic-coated, which container is closed with a metering valve. Canisters lined with a fluorocarbon polymer (especially polytetrafluoroethylene (PTFE)) in combination with a non-fluorocarbon polymer (especially polyethersulphone (PES) are preferred. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK356, BK357) and 3M-Neotechnic Ltd, UK (e.g. Spraymiser™).

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquified propellant is pressure filled through the charge vessel into a manufacturing vessel. The drug suspension is mixed before recirculation to a filling machine and an aliquot of the drug suspension is then filled through the metering valve into the canister. Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 500 micrograms medicament per puff.

Administration of medicament may be indicated for the treatment of mild, moderate or severe acute or chronic symptoms or for prophylactic treatment. It will be appreciated that the precise dose administered will depend on the age and condition of the patient, the particular particulate medicament(s) used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1,2,3 or 4 puffs each time.

Suitable daily doses may be, for example, in the range 50 to 200 microgram of salmeterol, depending on the severity of the disease and, for example, each valve actuation may deliver 25 microgram salmeterol. Typically each filled canister for use in a metered dose inhaler contains 60, 120, 200 or 240 metered doses or puffs of medicament.

The filled canisters and metered dose inhalers described herein comprise further aspects of the present invention.

A still further aspect of the present invention comprises a method of treating respiratory disorders such as, for example, asthma or chronic obstructive pulmonary disease (COPD), which comprises administration by inhalation of an effective amount of a formulation as herein described.

There follows a brief description of the Figures:

FIGS. 8 to 11 are DSC profiles and XRD patterns showing a mixed phase status of Polymorph I and II of salmeterol xinafoate, obtained by varying the operating conditions in Example 2.

FIGS. 24A and 24B show schematic designs of alternative apparatuses.

Figure 26:
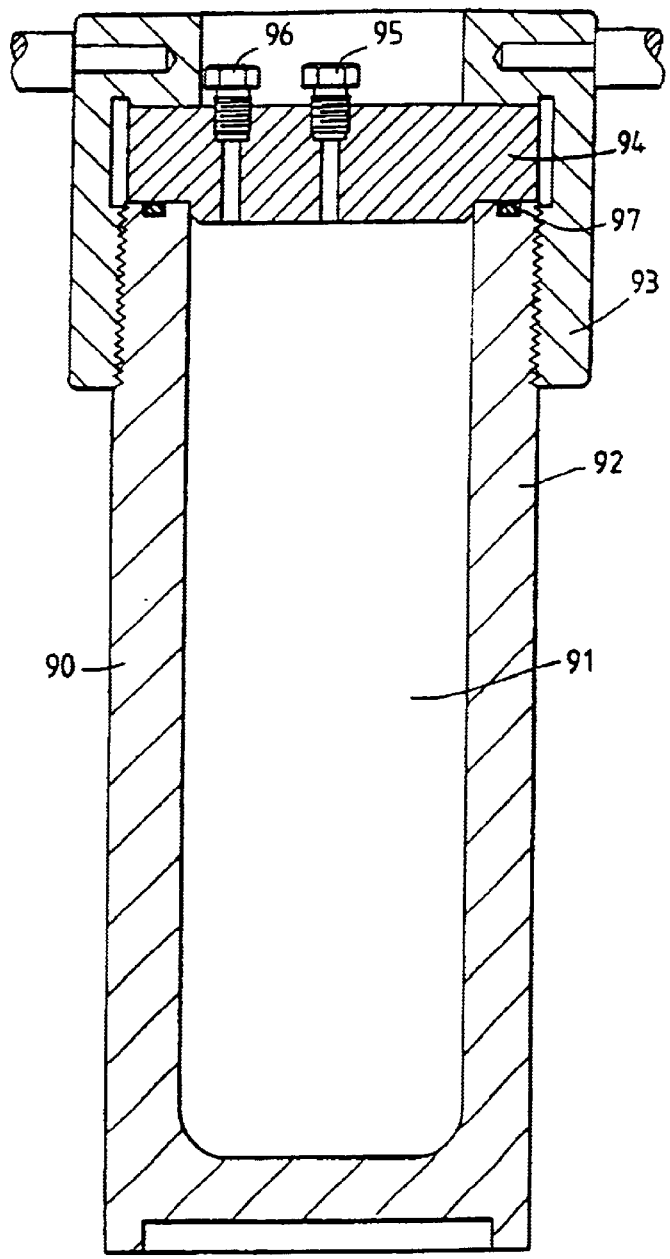
FIG. 26 is a longitudinal cross-section through a particle formation vessel.
Figure 27A:
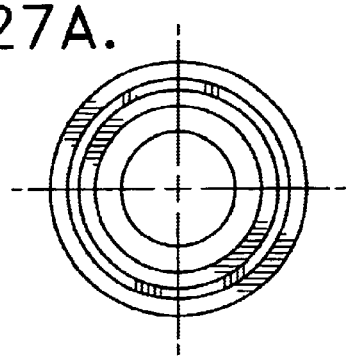
Figure 27B:
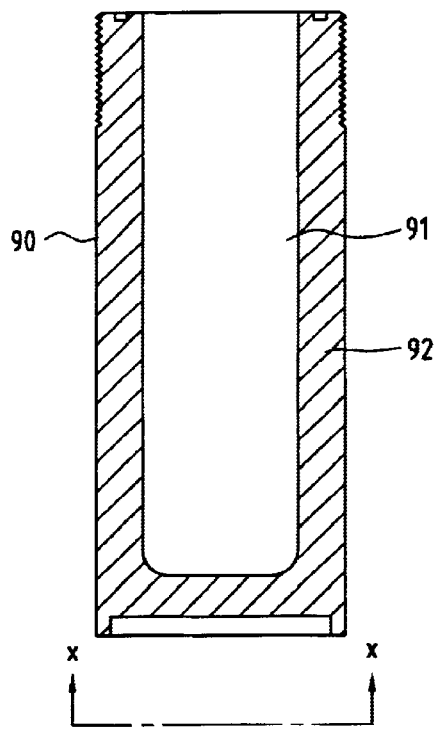
Figure 27D:
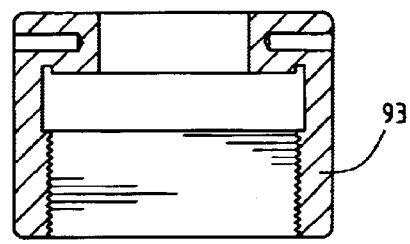
Figure 27E:
Figure 27F:
Figure 27C:
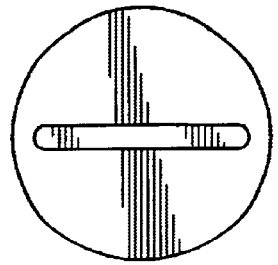

FIGS. 27A–F show the components of the vessel of FIG. 26.

Figure 28:
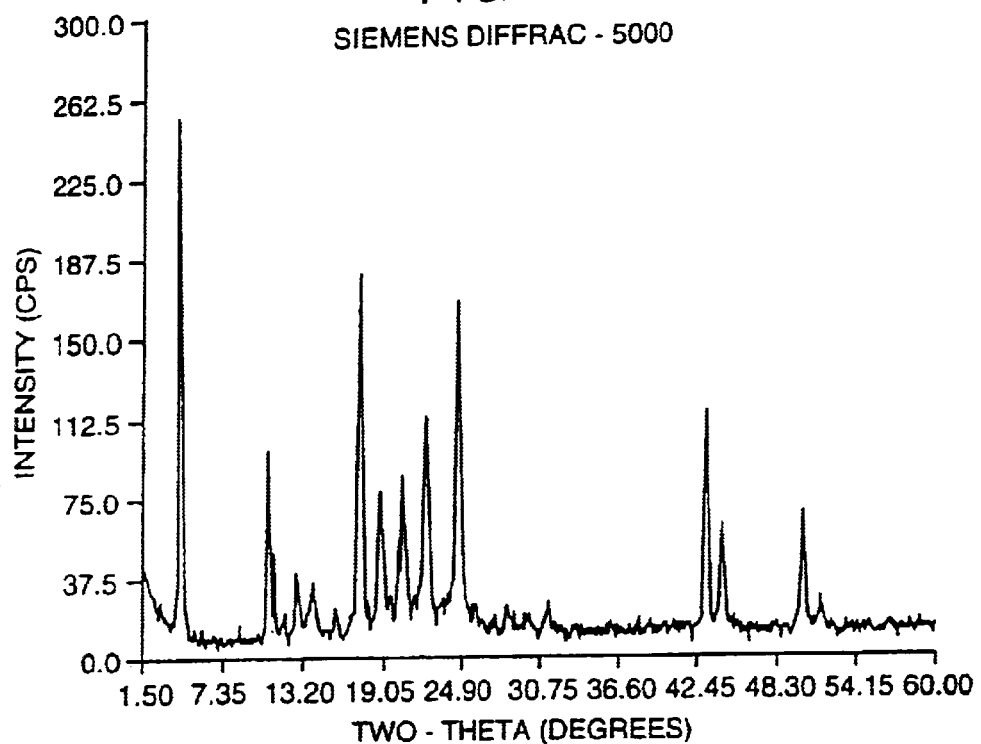

FIG. 28 is an XRD pattern for the salmeterol xinafoate prepared according to Example 6.

Figure 29:
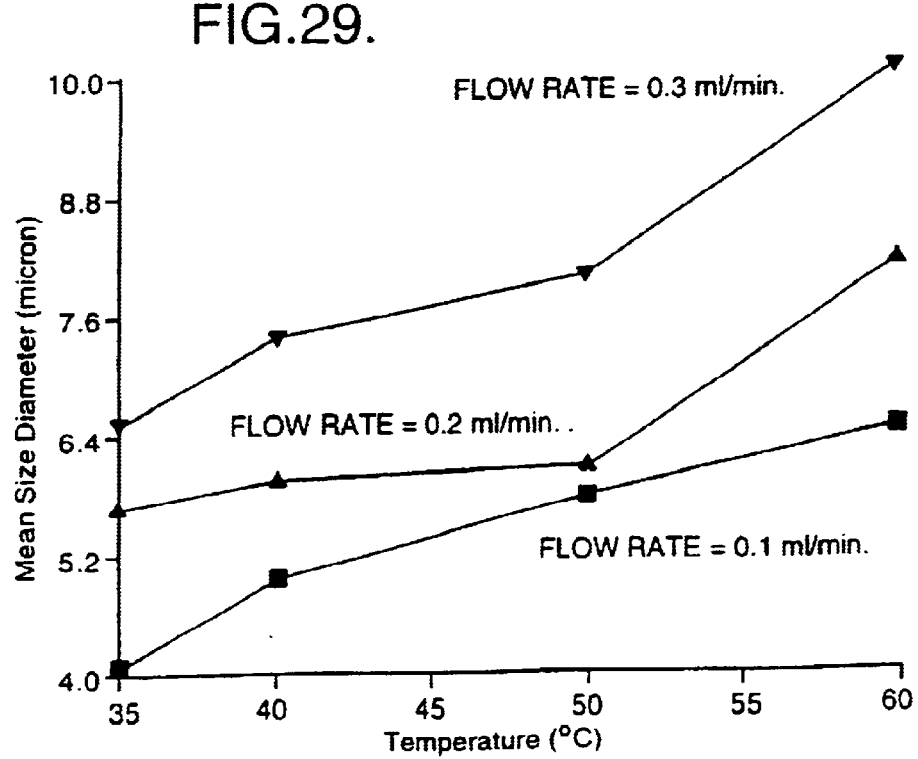
Figure 30:
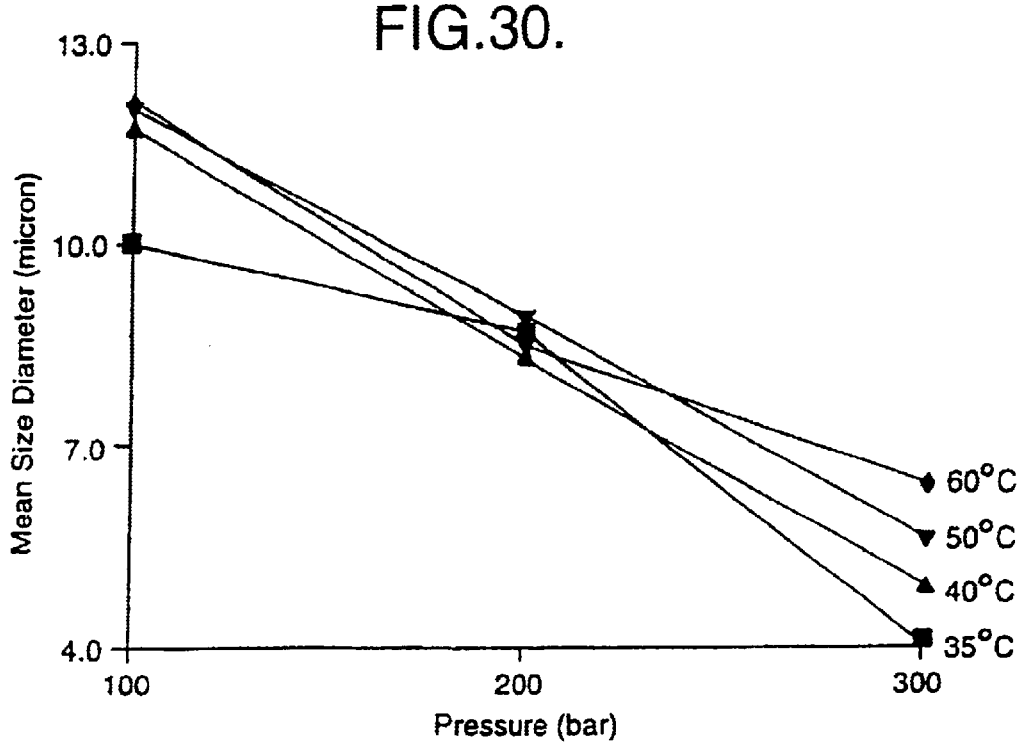
Figure 31:
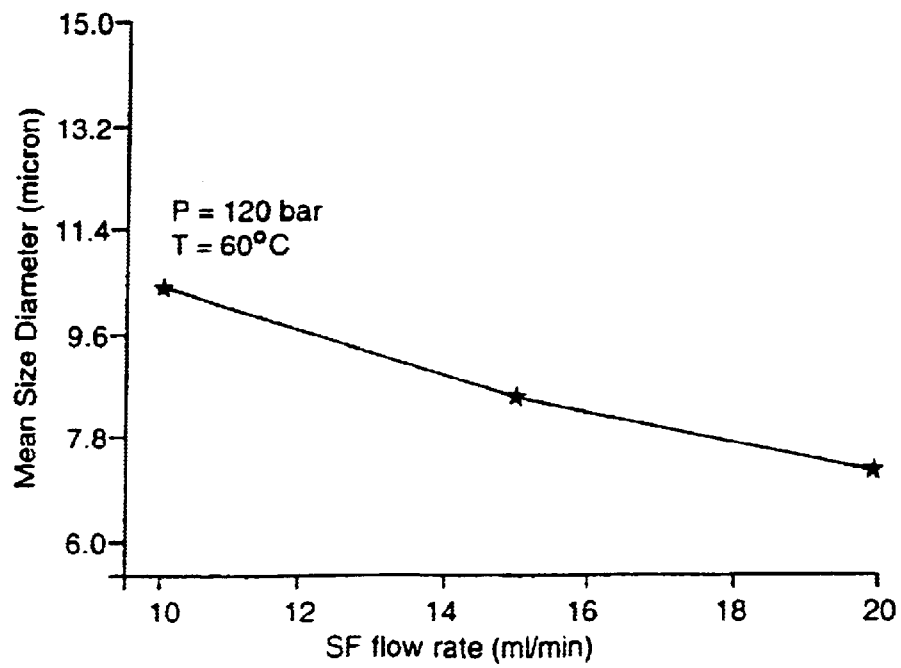

FIGS. 29–31 are graphs showing the effects of operating conditions on product particle size, when carrying out a method as described herein.

FIG. 32 is an XRD pattern for salmeterol xinafoate prepared according to Example 8.

Figure 34:
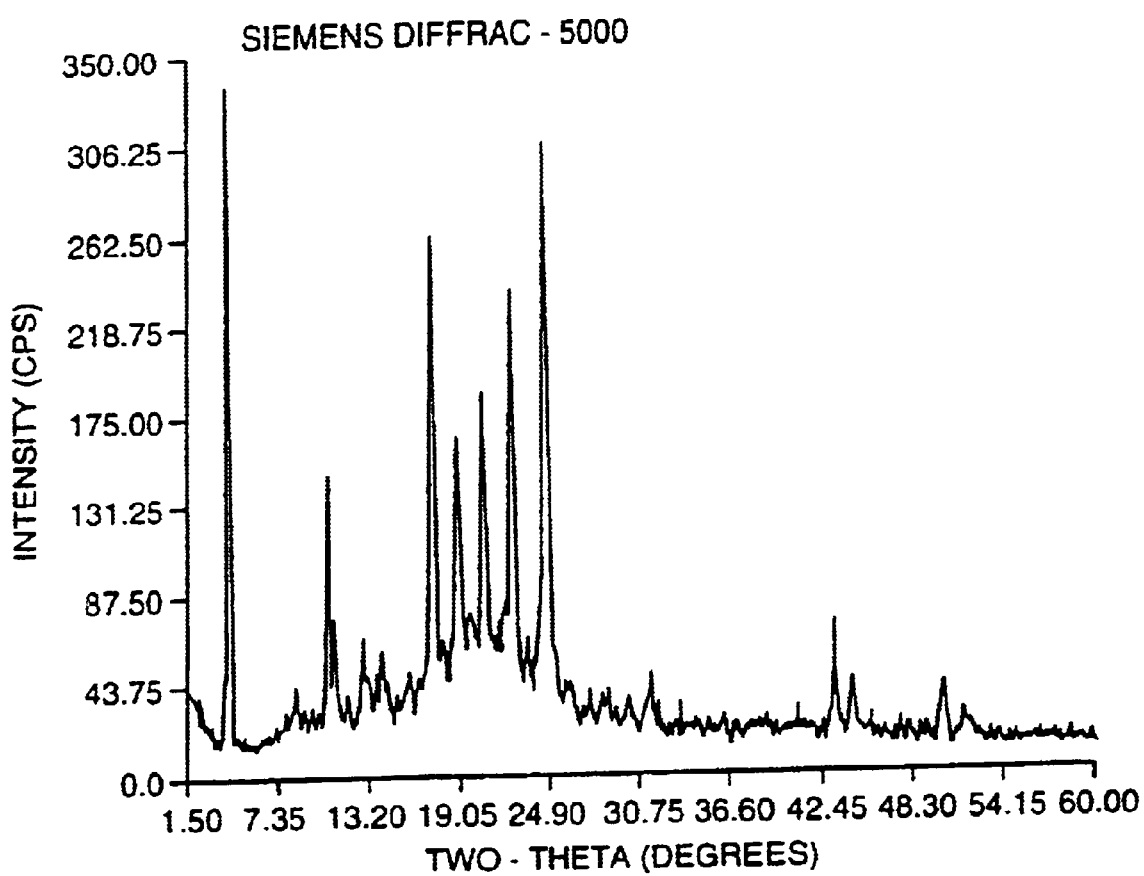

FIGS. 33 and 34 are XRD patterns for matrices of salmeterol xinafoate and hydroxypropylcellulose prepared according to Example 10.

Figure 35:
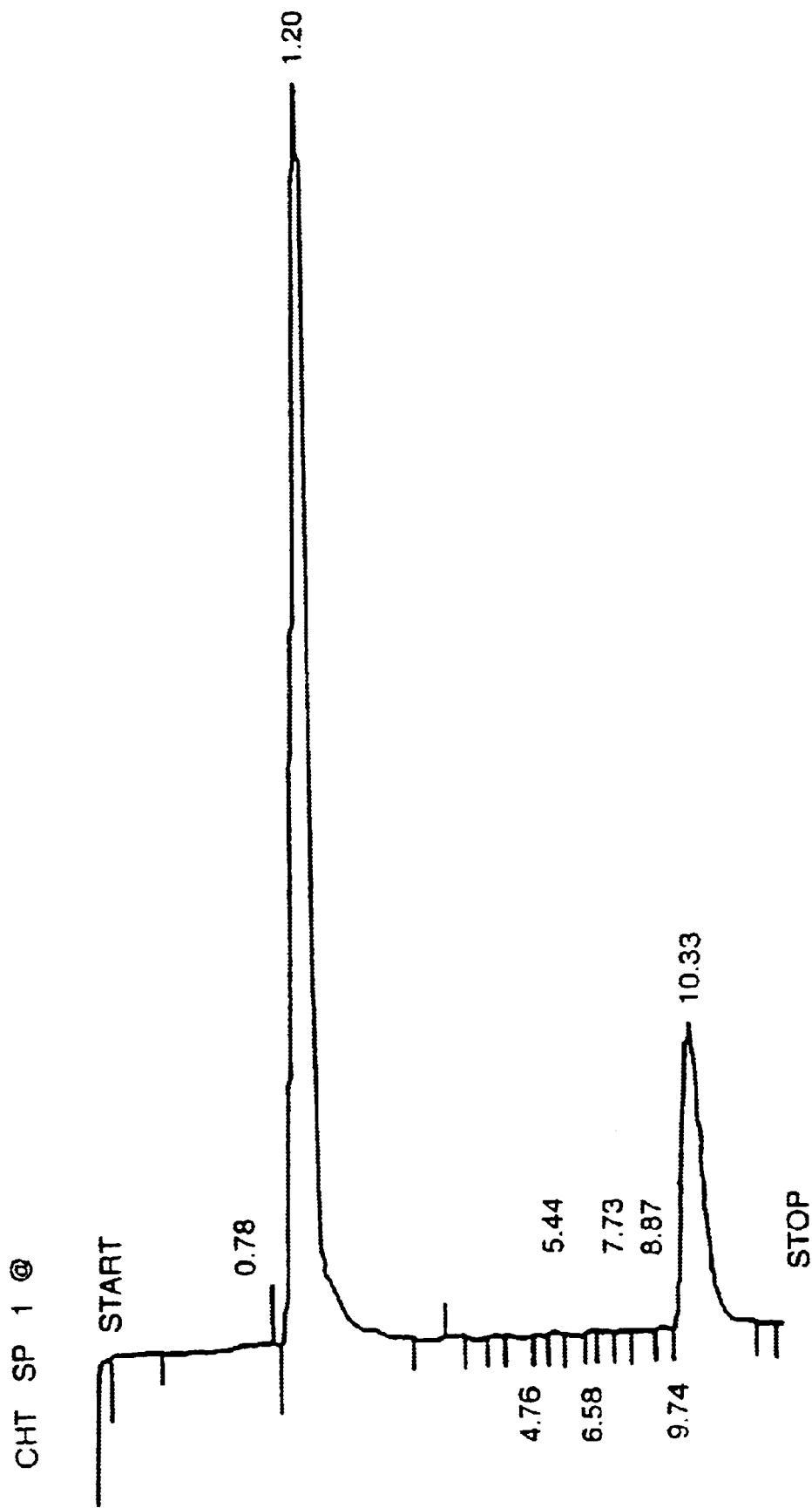
Figure 36:
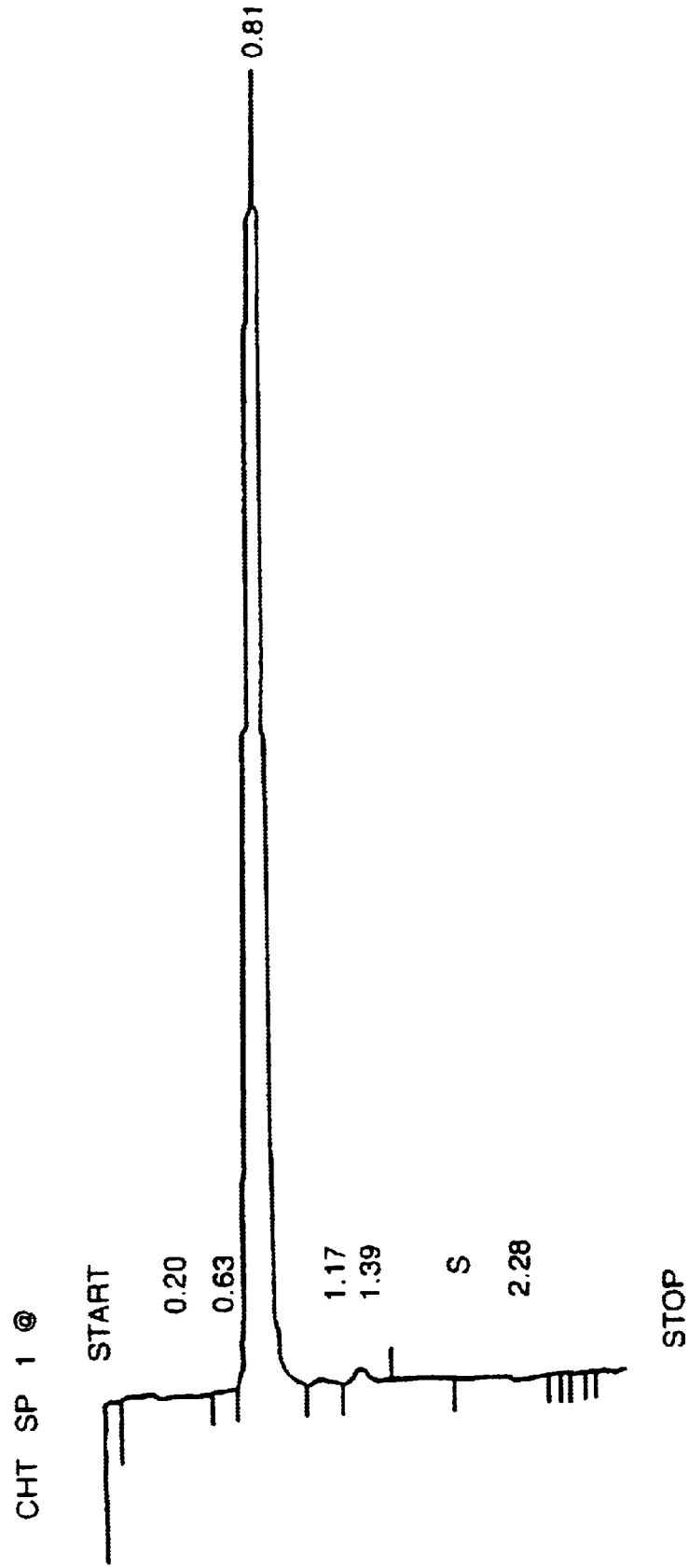

FIGS. 35 and 36 are HPLC chromatograms for pure salmeterol xinafoate and pure salicylic acid respectively, as used in Example 12.

Figure 37:
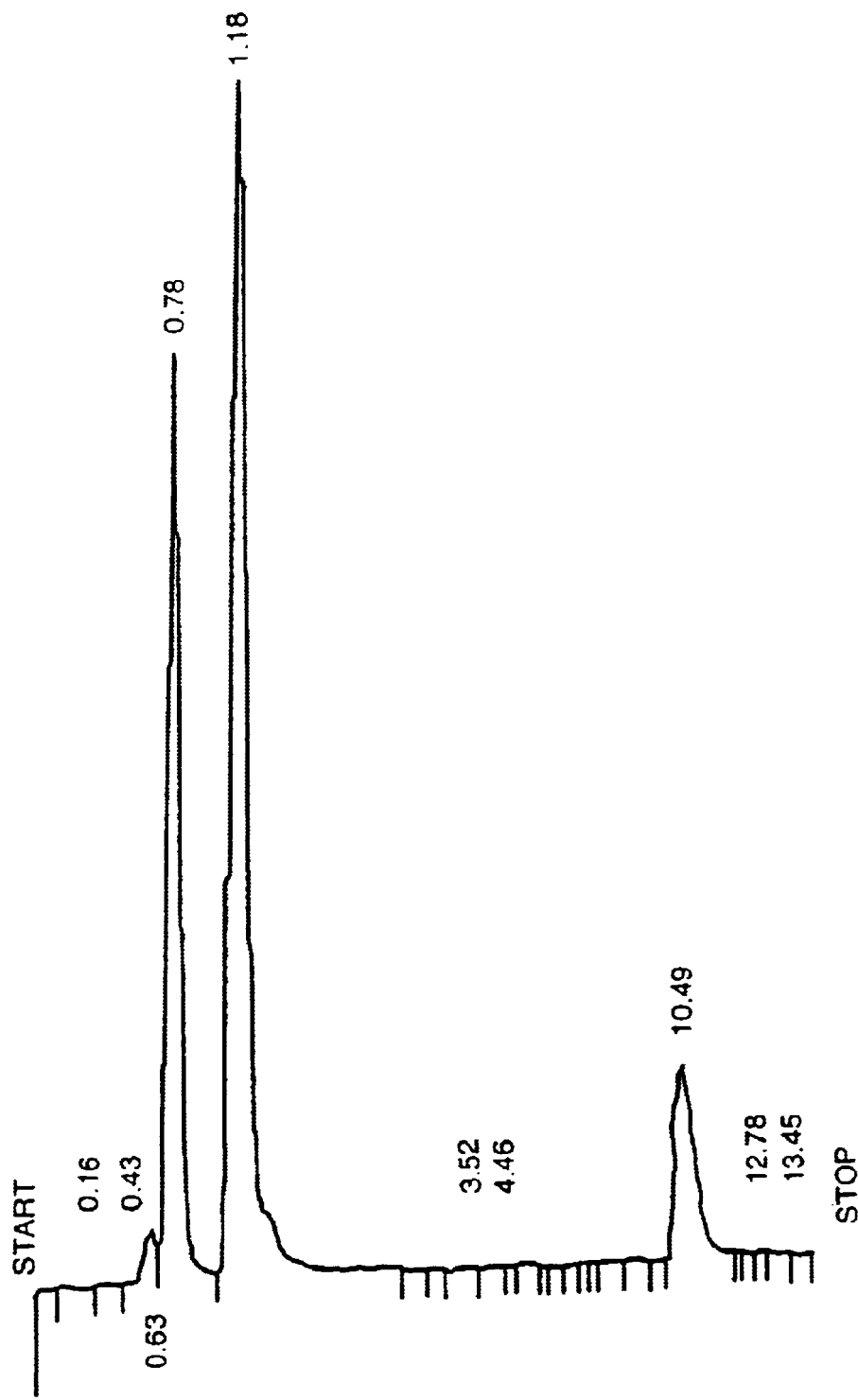

FIG. 37 is a HPLC chromatogram for the sample of salmeterol xinafoate and salicylic acid used in Example 12.

Figure 38:
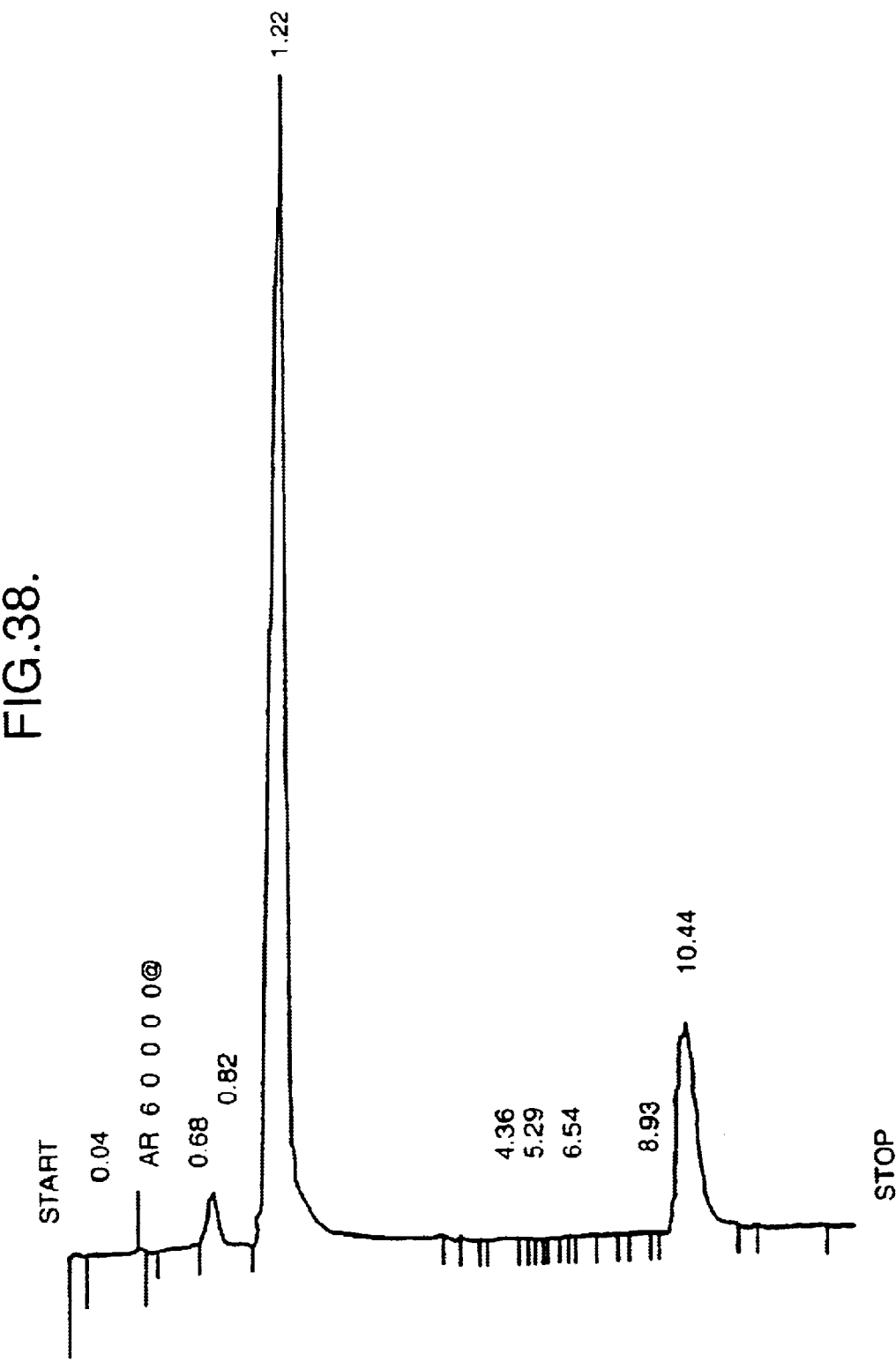

FIG. 38 is a HPLC chromatogram for the product prepared according to Example 12.

Figure 39:
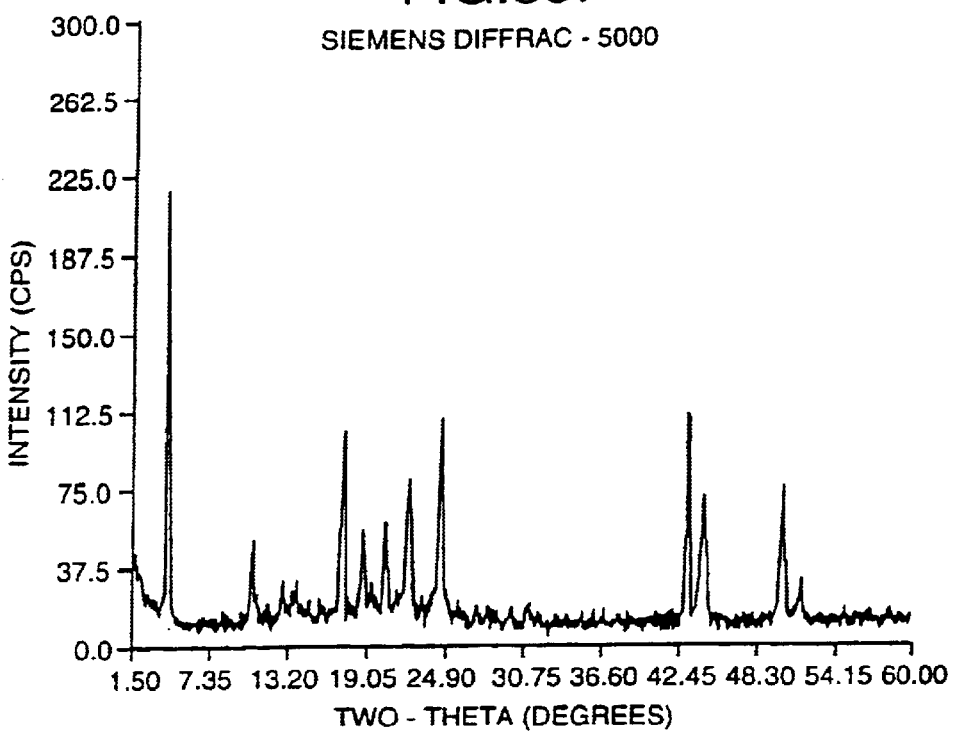
Figure 40:
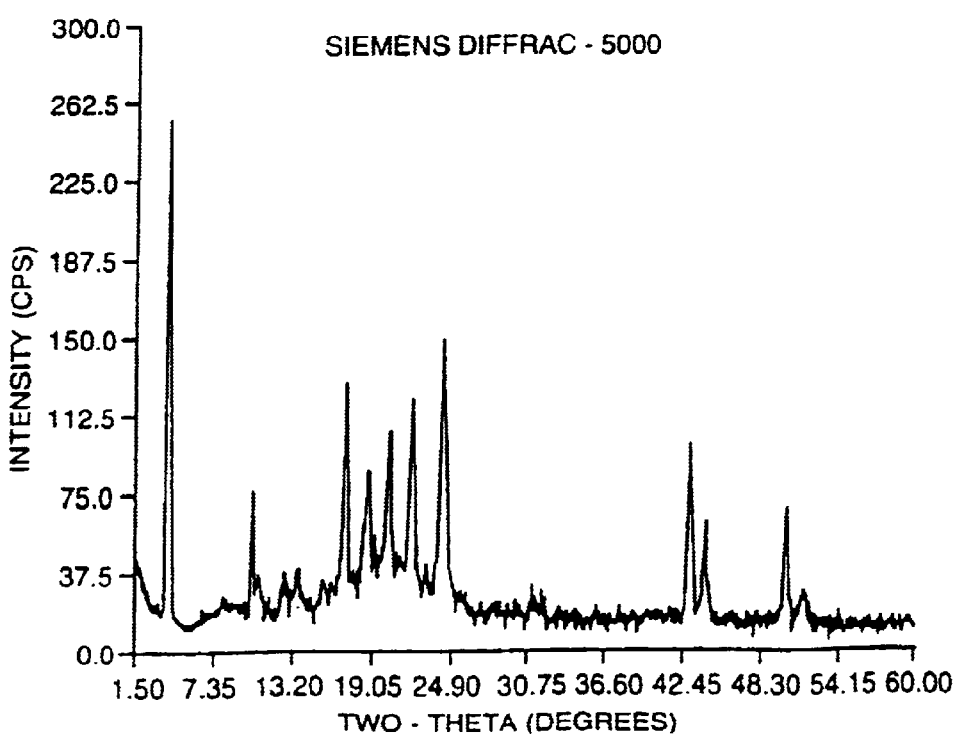

FIGS. 39 and 40 are XRD patterns for matrices of salmeterol xinafoate and hydroxypropylcellulose prepared according to Example 13.

Figure 41:
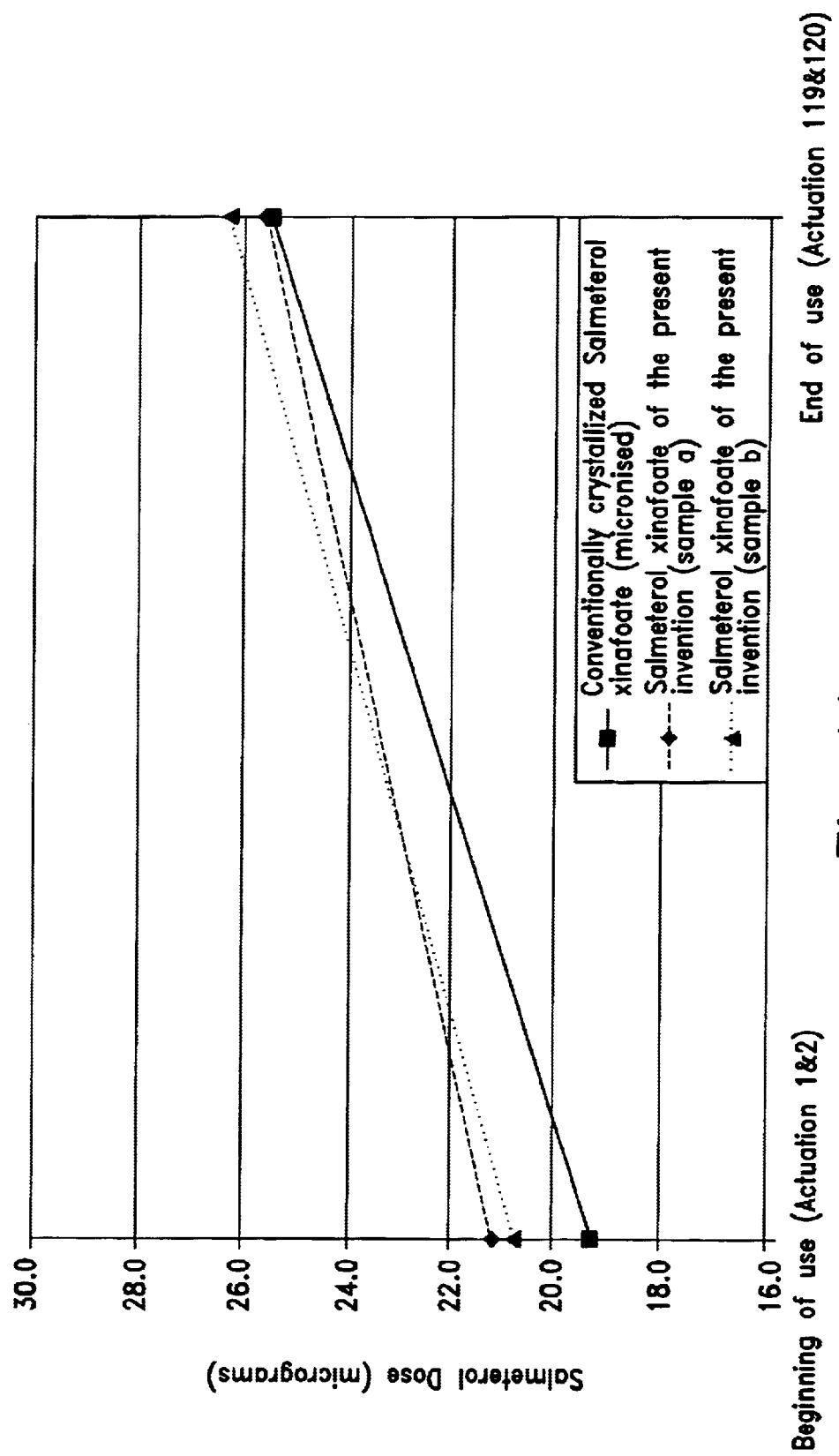

FIG. 41 shows dosing profiles for formulations of the present invention and a formulation containing micronised drug, presenting the Dose Delivered Through Use data of Example 15.

In the apparatus described herein, the means for the co-introduction of the supercritical fluid and the vehicle (containing at least one substance in solution or suspension) into the particle formation vessel preferably comprises a nozzle the outlet end of which communicates with the interior of the vessel, the nozzle having coaxial passages which terminate adjacent to one another at the outlet end, at least one of the passages serving to carry a flow of the supercritical fluid, and at least one of the passages serving to carry a flow of the vehicle in which a substance is dissolved or suspended.

Preferably, the opening at the outlet end (tip) of the nozzle will have a diameter in the range of 0.05 to 2 mm, more preferably between 0.1 and 0.3 mm, typically about 0.2 mm. The angle of taper of the outlet end will depend on the desired velocity of the fluids introduced through the nozzle; an increase in the angle may be used, for instance, to increase the velocity of the supercritical fluid introduced through the nozzle and hence to increase the amount of physical contact between the supercritical fluid and the vehicle. Typically (although not necessarily) the angle of taper will be in the range of about 10° to about 50°, preferably between about 20° and about 40°, more preferably about 30°. The nozzle may be made of any appropriate material, for example stainless steel.

In one embodiment, the nozzle has two coaxial passages, an inner and an outer. In another, preferred, embodiment, the nozzle has three coaxial passages, an inner, an intermediate and an outer. This latter design allows greater versatility in use of the apparatus, since if necessary two vehicles may be introduced into the particle formation vessel with the supercritical fluid. Improved dispersion and finer particles can also be obtained if such a nozzle is used to introduce a flow of the vehicle sandwiched between an inner and an outer flow of the supercritical fluid, since this ensures that both sides of the vehicle are exposed to the supercritical fluid. It is, however, to be appreciated that the nozzle may have any appropriate number of coaxial passages.

The internal diameters of the coaxial passages may be chosen as appropriate for any particular use of the apparatus. Typically, the ratio of the internal diameters of the outer and the inner passages may be in the range of from 2 to 5, preferably between about 3 and 5. Where an intermediate passage is included, the ratio of the internal diameters of the outer and intermediate passages may be in the range of from 1 to 3, preferably between about 1.4 and 1.8.

Particular examples of such coaxial nozzles and their typical dimensions are illustrated in FIGS. 2A, 2B and 25.

The temperature of the particle formation vessel may be maintained (preferably ±0.1° C.) by means of a heating jacket or, more preferably, an oven. The pressure of the particle formation vessel is conveniently maintained (preferably ±2 bar) by means of a back-pressure regulator. It will be appreciated that such apparatus will be readily available from, for example, manufacturers of supercritical fluid extraction equipment, for instance, from Jasco Inc., Japan.

There follows a detailed description of a preferred embodiment of the apparatus and method described herein with reference to FIGS. 1, 2, 24 and 25. FIGS. 1 and 24 are simplified diagrammatic flow sheets of apparatus, and FIGS. 2A, 2B and 25 show nozzles which may be used therein.

Referring to FIG. 1, the apparatus includes a particle formation vessel 6. This is typically a standard reaction vessel, for instance of the type available from Keystone Scientific Inc., of an appropriate capacity for the particular use to which it is to be put. The temperature and pressure of the vessel are maintained at constant desired level, by means of an oven 7 and back-pressure regulator 8, respectively.

In use, the system is initially pressurised and stable working conditions are met. A suitable gas, for example, carbon dioxide, is fed from source 1 via conduit 11 to a cooler 2, to ensure liquification, and is fed by conduit 12 to a pump 4. From there it is fed by conduit 13 to the vessel 6 via a nozzle 20. A solution or dispersion of a solid of interest, for example, salmeterol xinafoate, in a suitable vehicle, for example methanol, is drawn from source 5 by a conduit 14 to a pump 13 and is fed by conduit 15 to the vessel 6 via a nozzle 20.

The nozzle 20 may be as shown in either FIGS. 2 (A and B) or FIG. 25. That shown in FIG. 2 comprises coaxial inner and outer tubes 30 and 40, respectively. These define an inner passage 31 and an outer passage 41. The tubes 30 and 40 have conically tapering end portions 32 and 42, respectively. The tips of the end portions 32 and 42 define respective orifices 33 and 43, with the orifice 43 being a short distance downstream of the orifice 33. As indicated in FIG. 2B, the angle of taper of the end portion 42 is about 30° in this(non-limiting) example.

Figure 25:
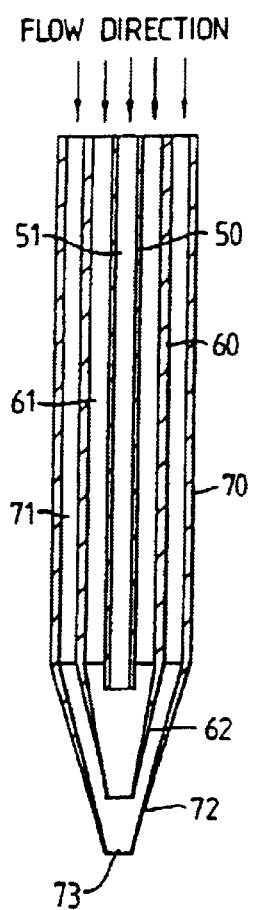
FIG. 25 shows a longitudinal section of the tip of an alternative coaxial nozzle.

The alternative nozzle illustrated in FIG. 25 comprises three coaxial tubes 50, 60 and 70 which define an inner passage 51, an intermediate passage 61, and an outer passage 71 respectively. Tubes 60 and 70 have conically tapering end portions 62 and 72, the angle of taper of the end portion 72 being about 30° in this example.

The nozzle of FIG. 25 allows three fluids to be introduced into the vessel 6 at the same time, leading to greater versatility in use of the apparatus. For instance, it is possible to add through one of the three passages a desired carrier or other additive intended to form part of, or be mixed with, the final particulate product. The additive is then dispersed simultaneously with the substance of primary interest. Also, in situ reactions may be carried out immediately prior to dispersion by the supercritical fluid, by introducing two or more reactants in two separate vehicles through two of the nozzle passages, the reaction occurring at the passage outlets either immediately prior to, or on, dispersion.

Alternatively, the nozzle of FIG. 25 may be used to introduce a flow of the vehicle (passage 61) sandwiched between an inner and an outer flow of the supercritical fluid (passages 51 and 71). This leads to improved dispersion of the vehicle, and hence to greater control over, and uniformity of, particle size in the final product; indeed it makes possible the formation of finer products than may be achieved using a two-passage nozzle.

In the nozzle shown, inner tube 50 has an internal diameter of 0.25 mm; intermediate tube 60 has an internal diameter of 0.53 mm; and outer tube 70 has an internal diameter of 0.8 mm and an outside diameter of 1.5 mm. The tip opening (73) has an internal diameter of 0.2 mm. The tubes are all made of stainless steel.

However, the nozzle may be made of any appropriate material and have any suitable dimensions. For instance, the internal diameters may be in the ranges 0.05–0.35 mm (inner); 0.25–0.65 mm (intermediate); and 0.65–0.95 mm (outer), preferably between 0.1 and 0.3 mm (inner); 0.3 and 0.6 mm (intermediate); and 0.7 and 0.9 mm (outer). The tip opening is likely to have an internal diameter in the range of 0.1–0.3 mm, preferably between 0.18 and 0.25.

In the apparatus of FIG. 1, the supercritical fluid is fed under pressure (at a high flow rate when compared with the flow rate of the vehicle) through for example the inner nozzle passage 31 of the nozzle shown in FIG. 2, and the solution or suspension of the solid of interest in a vehicle (hereinafter referred to as the "liquid") is simultaneously fed under pressure through the outer passage 41. It is believed that the high velocity supercritical fluid emerging from the orifice 33 causes the liquid emerging from the end of outer passage 41 to be broken up into droplets from which the vehicle is substantially simultaneously extracted by the supercritical fluid to result in the formation of particles of the solid previously held in the vehicle. It is to be understood, however, that although it is believed that this is what occurs, we do not wish to be bound by this theoretical explanation, and the actual physical processes occurring may not be precisely as just indicated.

Also, although the configuration has been described in which the supercritical fluid passes through the inner passage 31 and the vehicle passes through the outer passage 41, the configuration may be reversed, with the supercritical fluid in the outer passage 41 and the vehicle in the inner passage 31. Similarly in the nozzle of FIG. 25, any one of the three passages may be used to carry any one of a number of desired fluids, as appropriate.

The nozzle 20 ensures dispersion of the vehicle containing the solid of interest by the shearing action of the high velocity supercritical fluid and also thorough mixing of the dispersed vehicle with the supercritical fluid which simultaneously extracts the vehicle from the dispersed liquid, resulting in substantially immediate particle formation of the solid of interest. Because the supercritical fluid and vehicle are introduced coaxially, and dispersion occurs substantially simultaneously with vehicle extraction, a very high degree of control is possible of the conditions (e.g. pressure, temperature and flow rate) affecting particle formation, at the exact time when it occurs.

The particles formed are retained in the particle formation vessel by collecting means 21. The resultant supercritical solution is fed by conduit 16 to a back-pressure regulator 8 and is then fed by conduit 17 to a separation vessel 9 where it expands to cause the supercritical fluid to separate as a gas from the liquid vehicle. The gas may be fed by conduit 18 to a tank 10 and returned by conduit 19 to the cooler 2. The vehicle may also be collected for subsequent re-use. Means, not shown, may be provided to smooth the flow pulse of fluids and vehicles produced by pumps 3 and 4, so as to eliminate, or at least reduce, any flow pulsations.

When sufficient particle formation has occurred in the vessel 6, it is flushed through with clean, dry supercritical fluid, so as to ensure removal of any residual vehicle. The vessel can then be depressurised and particulate product removed.

The alternative apparatuses shown schematically in FIGS. 24A and 24B are for use in continuous particle formation. That shown in FIG. 24A includes two particle formation vessels 6*a* and 6*b*, each of the type shown in FIG. 1 and each including an inlet nozzle 20 and a particle collecting means (such as a filter) 21. Oven 7 serves both vessels.

In the apparatus in FIG. 24A, valve A controls the supply of the supercritical fluid and the vehicle (containing the substance of interest) to the two vessels 6*a* and 6*b*, and one-way valves E and F control the outlets from the two vessels to the back-pressure regulator 8. Valve D controls the supply of the vehicle to valve A. Valves B and C are needle valves, and items 80 and 81 are vents.

The apparatus may be "continuously" operated as follows. Valve A is firstly set to supply fluids to vessel 6*a*, in which particle formation is allowed to occur, as described in connection with FIG. 1. Valve E is set so that the resultant supercritical solution may drain from vessel 6*a* to the back-pressure regulator 8 for subsequent recycling.

When sufficient particle formation has occurred, valve D is closed to stop the flow of vehicle, whilst the supercritical fluid continues to flow through vessel 6*a* to dry (flush) the products. Valve A is then set to supply fluids to the empty vessel 6*b* and valve D re-opened, whilst valve B is opened so as slowly to depressurise vessel 6*a*. One-way valve E eliminates any chance of a back-flow from vessel 6*b* or of disruption of the particle formation process now occurring in vessel 6*b*. Vessel 6*a* is removed for collection of the product, and then refitted and repressurised ready for re-use. Supercritical solution drains from vessel 6*b* via valve F, which is set appropriately.

Once particle formation in vessel 6*b* is complete, the valves are set back to allow it to continue in vessel 6*a*, whilst 6b is flushed and emptied. In this way, particle formation in the apparatus can continue uninterrupted.

The apparatus shown in FIG. 24B includes only one particle formation vessel 6, which does not contain any particle collecting means, and two particle collection vessels 25a and 25b downstream of vessel 6. The supercritical fluid carries the formed particles to the collection vessels 25a and 25b.

The apparatus also includes an inlet nozzle 20, two vents 26, a back pressure regulator 27, an oven 7 and valves A–H. Supercritical fluid and solution (vehicle) are fed to the nozzle 20 where shown.

The apparatus might be used as follows. Initially, (valves C, D, E, and F closed) the system is pressurised and stable working conditions are met; valves B and H are then closed, driving the flow of supercritical fluid through valve A only. The vehicle and substance of interest are introduced into vessel 6 and the particles formed are transported by the supercritical fluid via valve A to collection vessel 25a which contains a particle retention device. The retention device is placed at the outlet of the vessel to ensure maximum collection volume. The solid-free supercritical solution (the supercritical fluid and the vehicle) flows across valve G to the back pressure regulator 27. On emerging from the back pressure regulator the supercritical solution expands into a large pressure resistant vessel (not shown), where the vehicle separates from the gas and both can be recycled.

When the collection vessel 25a is full, switching takes place, closing valves A and G and simultaneously opening valves B and H. This allows the flow of the supercritical solution, emerging from vessel 6, into the second collection vessel 25b. Valves C and G are opened after flow switching to ensure a high flow of supercritical fluid to flush the full collection vessel 25a, i.e. the supercritical solution volume is replaced by a supercritical fluid volume. It is estimated that 1–2 times the volume of the collection vessel, of the supercritical fluid, ensures a dry powder. The flushing time is generally short owing to the fact that the particles are occupying the volume of the collection vessel. After flushing, valves C and G are closed and valve F (a needle valve) is slowly opened to depressurise the full collection vessel 25a. Since the particulate product takes up the vessel volume only a small amount of supercritical fluid is discharged, mainly the internal volume of the fittings involved.

The full collection vessel 25a is removed and the dry powder collected. After refitting and repressurising via valve C, the vessel is ready for re-use as soon as the second collection vessel 25b, which has meantime been collecting product from vessel 6, is full.

The benefits of using the apparatus of FIG. 24B include:
1. The elimination of depressurising and pressurising steps of the reaction vessel every time product is collected. This could mean considerable reductions in the amounts of fluids being discharged, in particular when using a large volume particle formation vessel (scaling up) or expensive high purity gases.
2. Significant time saving during the flushing (drying) procedure. In a batch particle formation process only a rather small volume of the reaction vessel is occupied by the product and the remaining volume (where dispersion takes place) is taken up by the supercritical solution. This mixture will eventually be replaced by at least the same volume of the supercritical fluid in the flushing procedure, which can therefore take a long time when scaled up.
3. The environment and workers are less exposed to the products during the recovery step. In some cases it is difficult to collect products directly from a large reaction vessel due to handling inconvenience or because the products of interest are light, oxygen or humidity sensitive which might affect their characteristics or purity.

The invention is further illustrated by the following non-limiting examples. Examples 1 to 5, illustrating the preparation of salmeterol xinafoate and its physical properties were carried out using apparatus substantially the same as that illustrated in FIGS. 1 and 2, using a 32 ml particle formation vessel and a two-passage coaxial nozzle having the following dimensions:

|  | outer diameter | inner diameter |
| --- | --- | --- |
| outer tube: | 1.58 mm | 0.75 mm |
| inner tube: | 0.63 mm | 0.20 mm |

The tip orifice (43 in FIG. 2B) was 0.32 mm in diameter, and both the inner and outer tubes were made of stainless steel.

EXAMPLE 1

Conventionally crystallised salmeterol xinafoate, both before and after micronisation, was compared against salmeterol xinafoate made by the supercritical fluid method described herein. A solution of salmeterol xinafoate in acetone (0.63% w/v) was co-introduced with $CO_2$ at 300 bar and 45° C. via a coaxial nozzle into the particle formation vessel using the apparatus described and shown in FIG. 1 to give sample 1. A solution of salmeterol xinafoate in acetone (0.50% w/v) was cointroduced with $CO_2$ at 100 bar and 55° C. via a coaxial nozzle into the particle formation vessel using the apparatus described and shown in FIG. 1 to give sample 2. In each case, the solution flow rate was 0.4 ml/min and supercritical $CO_2$ was co-introduced into the particle formation vessel at a flow rate of 9 ml/min.

The dynamic bulk densities are shown below in Table 2:

TABLE 2

| Sample | Dynamic Bulk Density W (g · cm$^{-3}$) |
| --- | --- |
| conventionally crystallised salmeterol xinafoate (non-micronised) | 0.312 |
| conventionally crystallised salmeterol xinafoate (micronised) | 0.137 |
| SCF salmeterol xinafoate (sample 1) | 0.033 |
| SCF salmeterol xinafoate (sample 2) | 0.059 |

The conventionally crystallised salmeterol xinafoate was prepared using the methodology described in International Patent Specification No. WO 92/09557.

EXAMPLE 2

Control of Formation of the Polymorphs of Salmeterol Xinafoate

Figure 1:
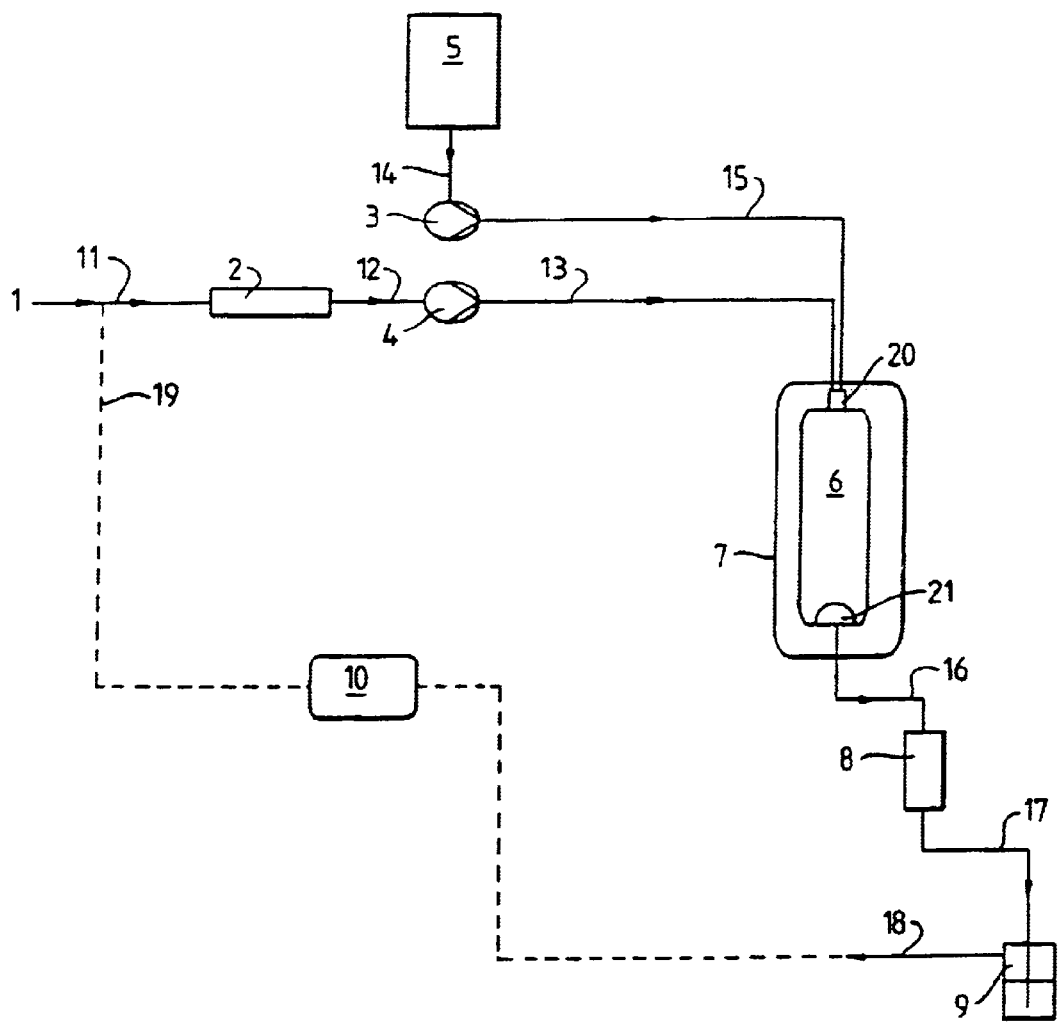
FIG. 1 shows a schematic design of an apparatus described herein.
Figure 4:
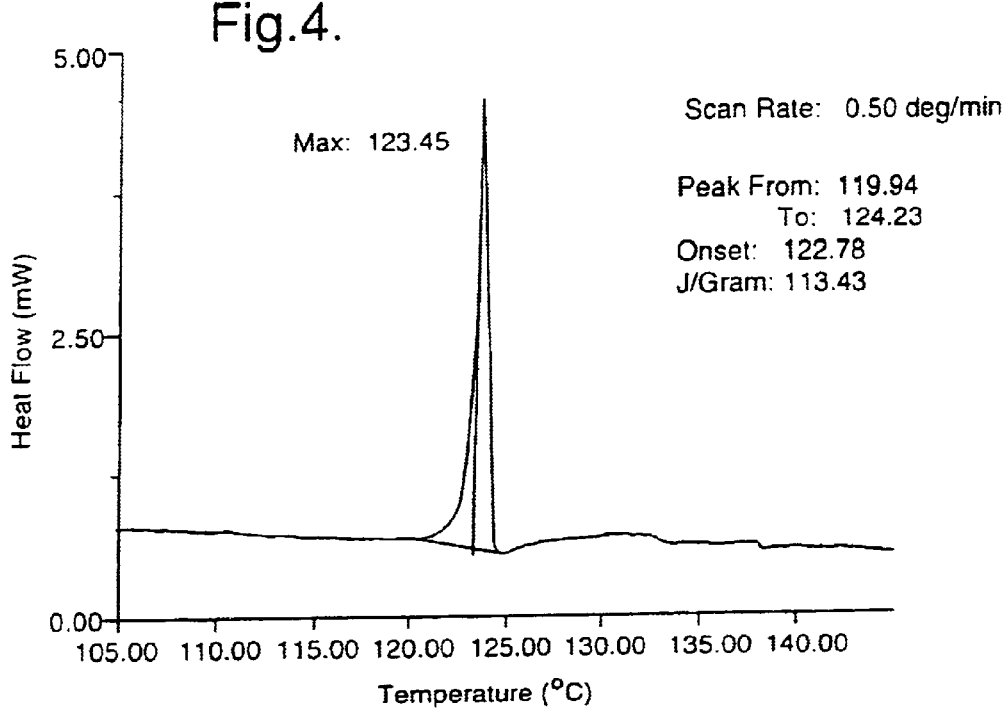
FIG. 4 is a DSC profile of Polymorph I of salmeterol xinafoate, as prepared in Example 2.
Figure 5:
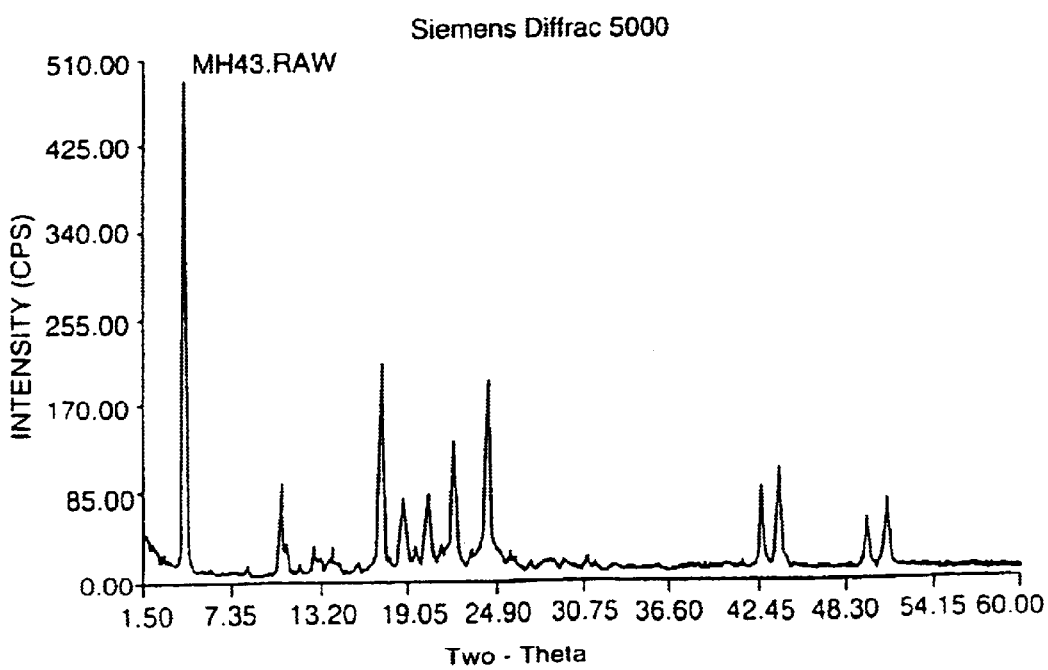
FIG. 5 is an X-ray powder diffraction (XRD) pattern of Polymorph II of salmeterol xinafoate, as prepared in Example 2.

A solution of salmeterol xinafoate in methanol (0.6% w/v) was co-introduced with $CO_2$ at 300 bar and 45° C. via a coaxial nozzle into the particle formation vessel using the apparatus described and shown in FIG. 1. A dry, easily handlable powder without significant static charge was formed. The product was characterised by differential scanning calorimetry (DSC) and by X-ray powder diffraction (XRD), and data are shown in FIGS. 4 and 5. A highly crystalline product with well defined melting point (peak heat flow=123.5° C.) was obtained. Major intensities in the XRD pattern were observed at 4.2, 17.3, and 24.5 degrees 2 theta. This material was defined as Polymorph I.

Figure 6:
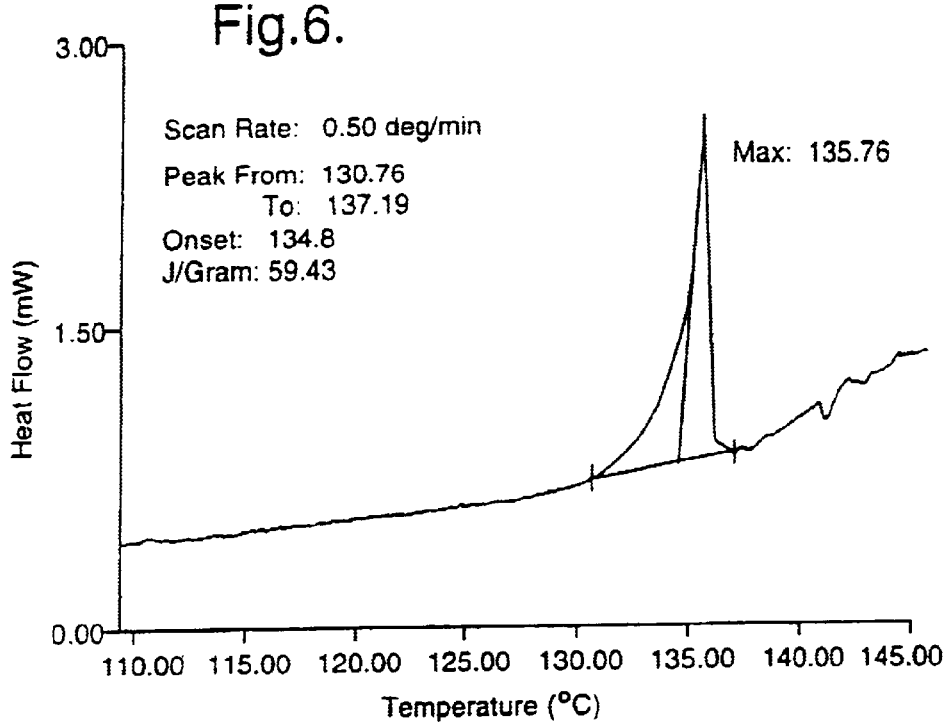
FIG. 6 is a DSC profile of Polymorph II of salmeterol xinafoate, as prepared in Example 2.
Figure 7:
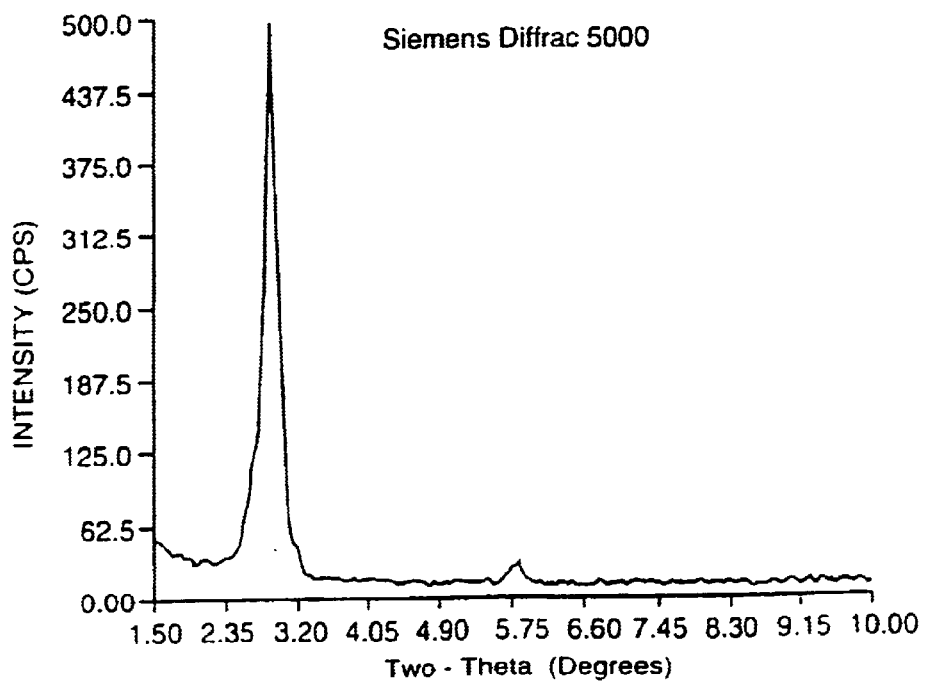
FIG. 7 is an expanded XRD pattern of Polymorph II of salmeterol xinafoate, as prepared in Example 2.
Figure 8:
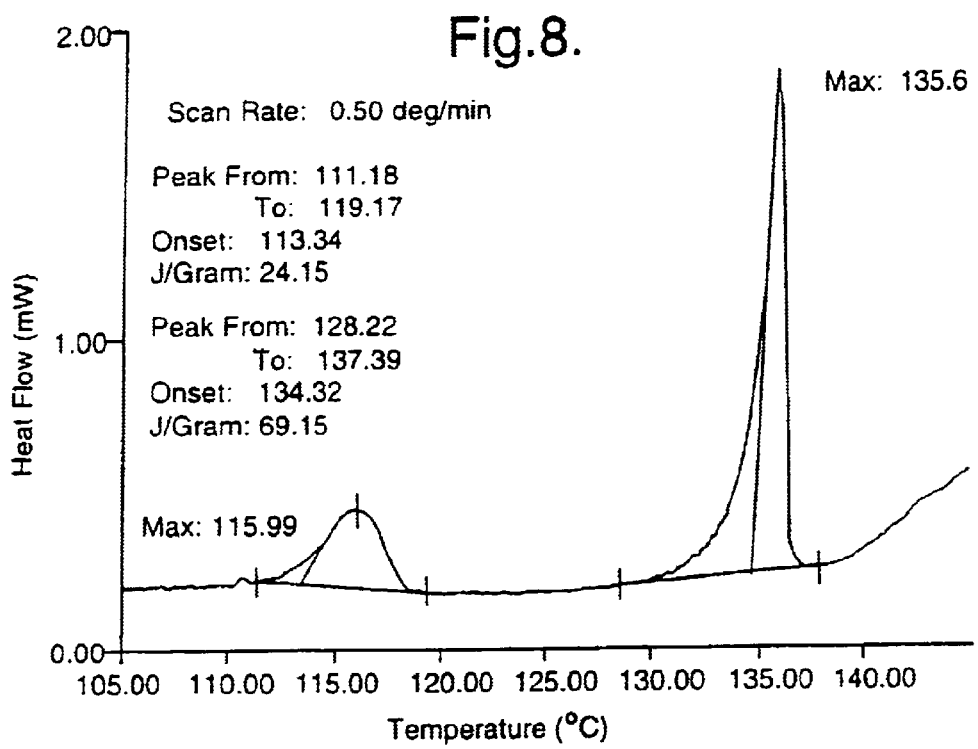
Figure 9:
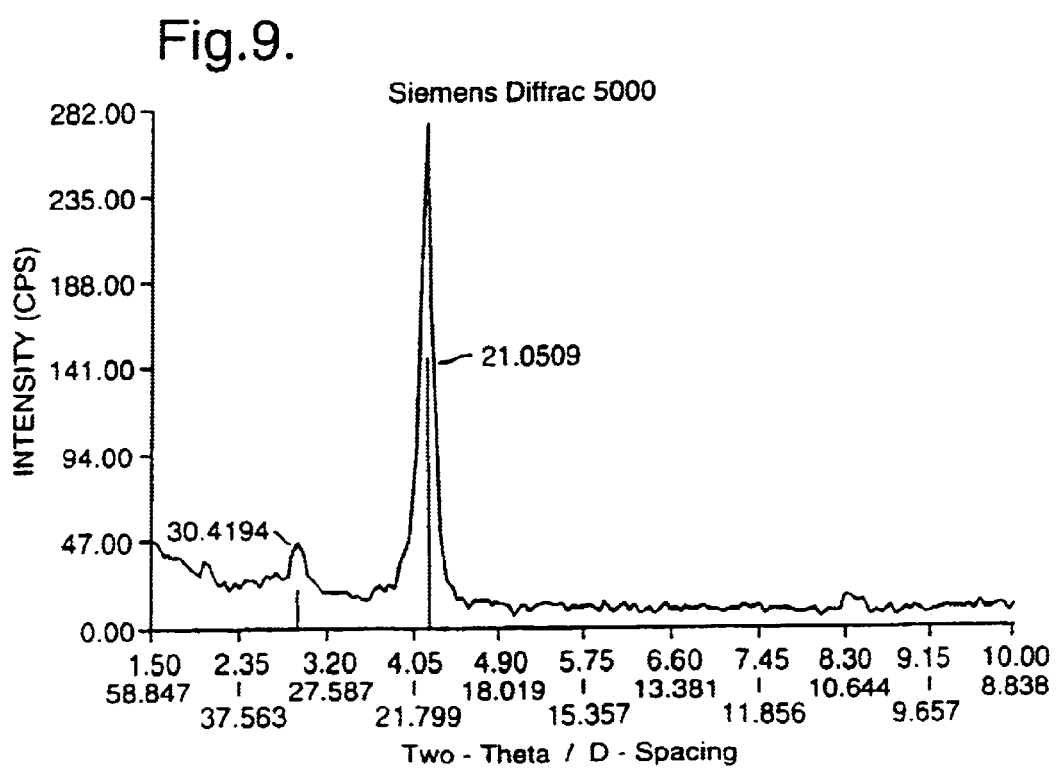
Figure 12:
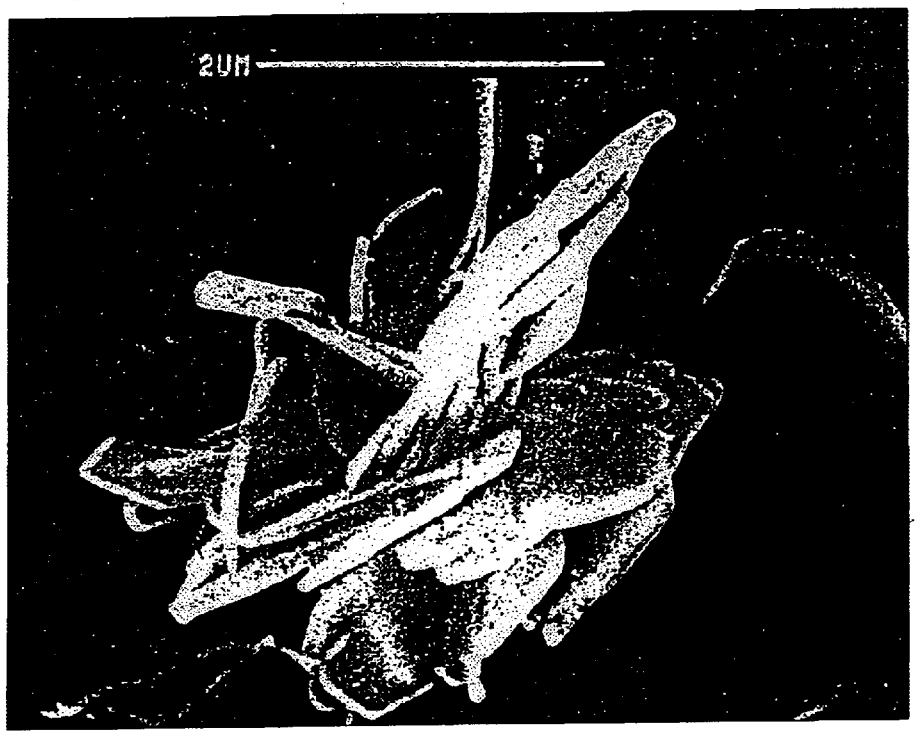
FIGS. 12 to 16 are scanning electron microscopy (SEM) photographs of salmeterol xinafoate, as prepared in Example 3.
Figure 13:
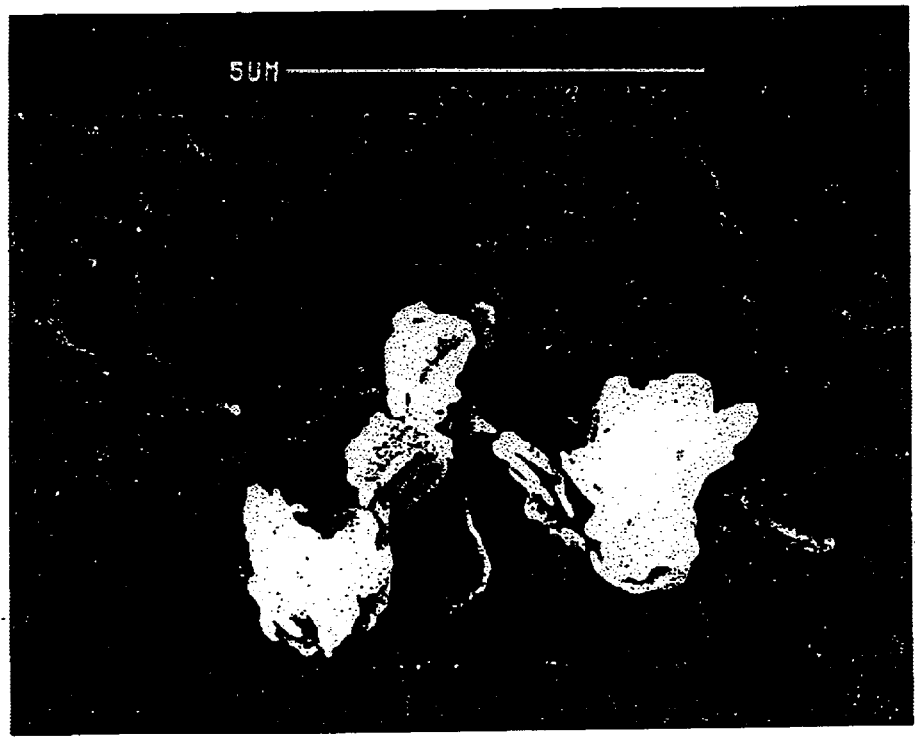
Figure 14:
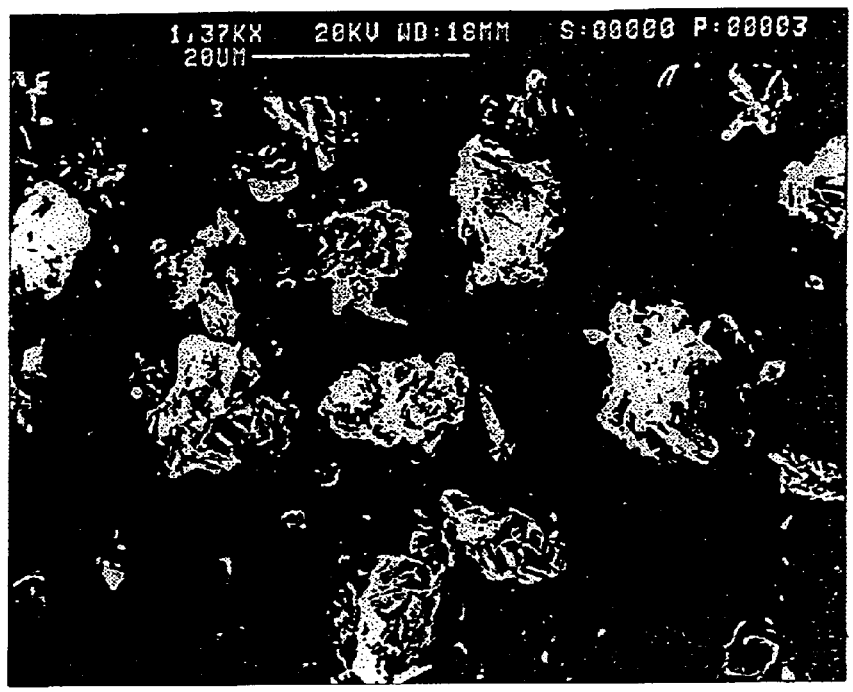
Figure 15:
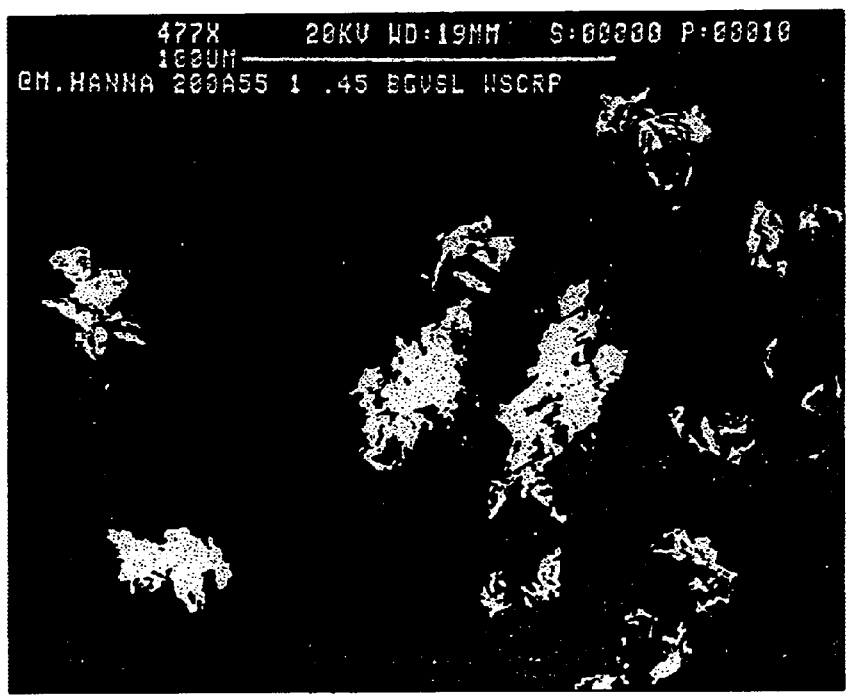

In another experiment, a solution of salmeterol xinafoate in acetone (0.6% w/v) was co-introduced with $CO_2$ at 250 bar and 90° C. via a coaxial nozzle into the particle formation vessel using the apparatus described and shown in FIG. 1. A dry, easily handlable powder without significant static charge was formed. The data from DSC and XRD are shown in FIGS. 6 and 7. A second polymorph was obtained, defined as Polymorph II. This form was crystalline with a well defined melting point (peak heat flow=135.8° C.). A different XRD pattern from Polymorph I was obtained with a new major intensity at 2.9 degrees 2 theta. The change in working conditions led to the formation of a pure, higher melting point phase (Polymorph II) which had previously only been observed, in prior known methods of preparing salmeterol xinafoate, after heating Polymorph I at temperatures which caused heat induced transition.

Controlled formation of mixtures of Polymorph I and Polymorph II was also achieved by varying the working conditions. DSC and XRD data (see FIGS. 8 to 11) confirm the mixed phase status of these products with increasing Polymorph II component as the working temperature was increased.

EXAMPLE 3

Control of Particle Size and Size Distribution

A solution of salmeterol xinafoate in acetone (0.6% w/v) was co-introduced with $CO_2$ at 200 bar and 55° C. via a coaxial nozzle into the particle formation vessel using the apparatus described and shown in FIG. 1. A series of products was obtained by changing the flow rate ratio of salmeterol xinafoate solution/supercritical $CO_2$, where the flow ratio is defined as:

$$\frac{\text{(flow rate of vehicle containing the solute)}}{\text{(flow rate of supercritical fluid)}}$$

The flow ratio was changed between 0.01 and 0.07, with a flow rate of 9 ml/min for the supercritical $CO_2$.

The resultant dry, easily handlable products without significant static charge were examined by scanning electron microscopy (SEM) and by laser diffraction (Malvern Mastersizer E) for particle size analysis (see FIGS. 12–15). It was found that by decreasing the flow rate ratio of salmeterol xinafoate solution/supercritical $CO_2$, finer particles were obtained (see FIGS. 12 and 13) than for higher fluid flow rate ratios (see FIGS. 14 and 15). The particle size analysis data is shown in Table 3 below.

TABLE 3

|  | Mean Particle Size ($\mu$m) | % < 5 $\mu$m | % < 10 $\mu$m | Uniformity index |
| --- | --- | --- | --- | --- |
| Conventionally crystallised salmeterol xinafoate (micronised) | 1–3 | Typically >90 | Typically >95 | 13.1 |
| SCF Salmeterol xinafoate (sample 1) | 3.85 | 66.0 | 94.5 | 10.2 |

TABLE 3-continued

|  | Mean Particle Size ($\mu$m) | % < 5 $\mu$m | % < 10 $\mu$m | Uniformity index |
| --- | --- | --- | --- | --- |
| SCF Salmeterol xinafoate (sample 2) | 18.84 | 5.7 | 16.1 | 19.2 |

The uniformity index is defined as:

$$100 \times \left[\frac{\text{particle size at 10\% cumulative undersize}}{\text{particle size at 90\% cumulative undersize}}\right]$$

Figure 16:
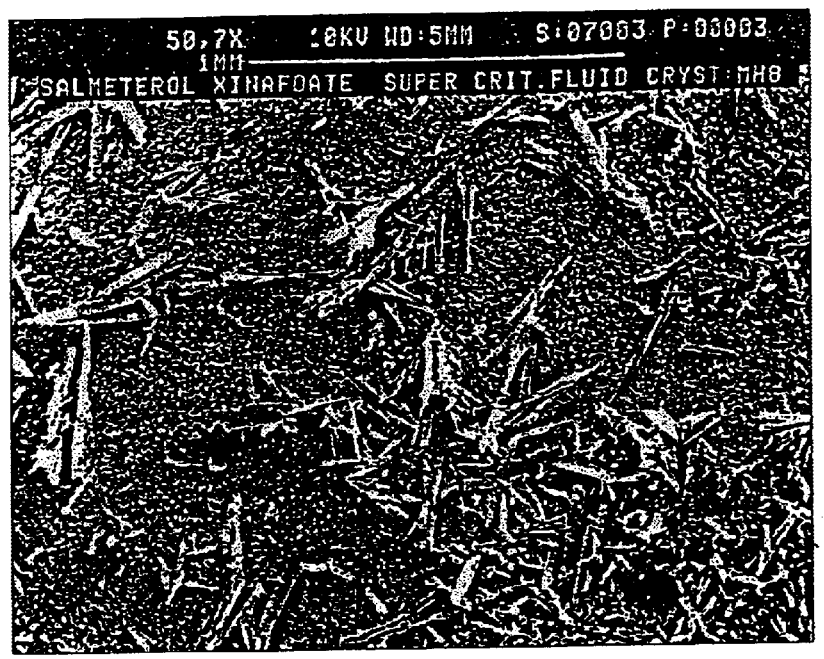

In another experiment, a solution of salmeterol xinafoate in isopropanol (0.2% w/v) was co-introduced with $CO_2$ at 150 bar and 60° C. via a coaxial nozzle into the particle formation vessel using the apparatus described and shown in FIG. 1. The dry, easily handlable product without significant static charge was examined by SEM (see FIG. 16) and found to be composed of needle shaped particles with a maximum particle dimension of up to 300 microns. Thus by controlling and changing the working conditions of the particle formation process, salmeterol xinafoate products composed of particles with different particle sizes and size distributions were produced.

EXAMPLE 4

Control of Particle Shape

Figure 17:
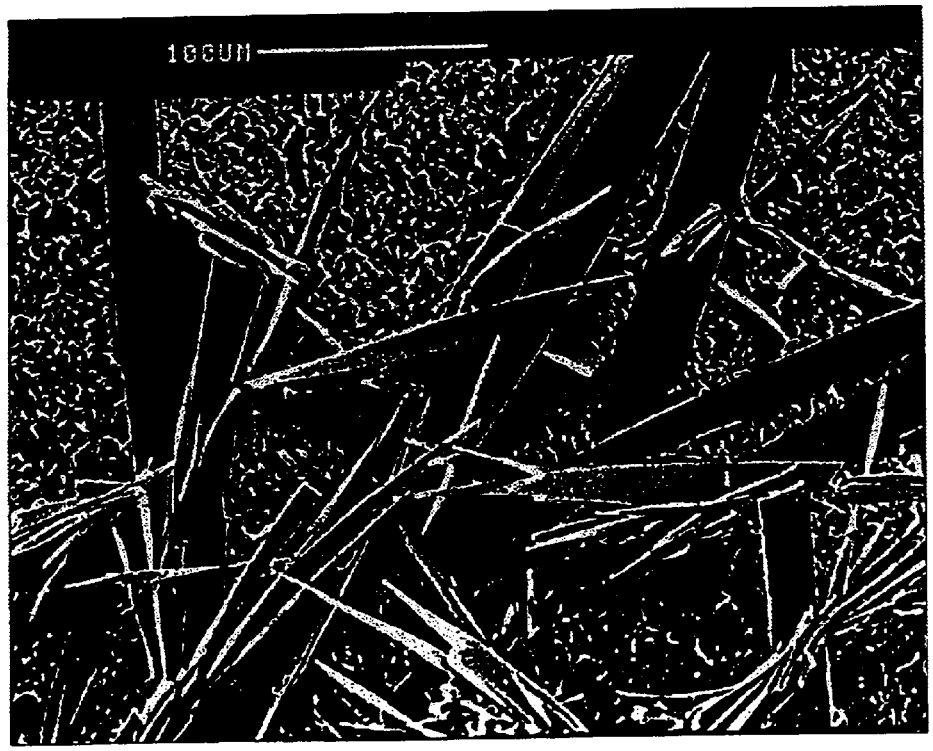
FIGS. 17 to 19 are SEM photographs of salmeterol xinafoate, as prepared in Example 4.
Figure 18:
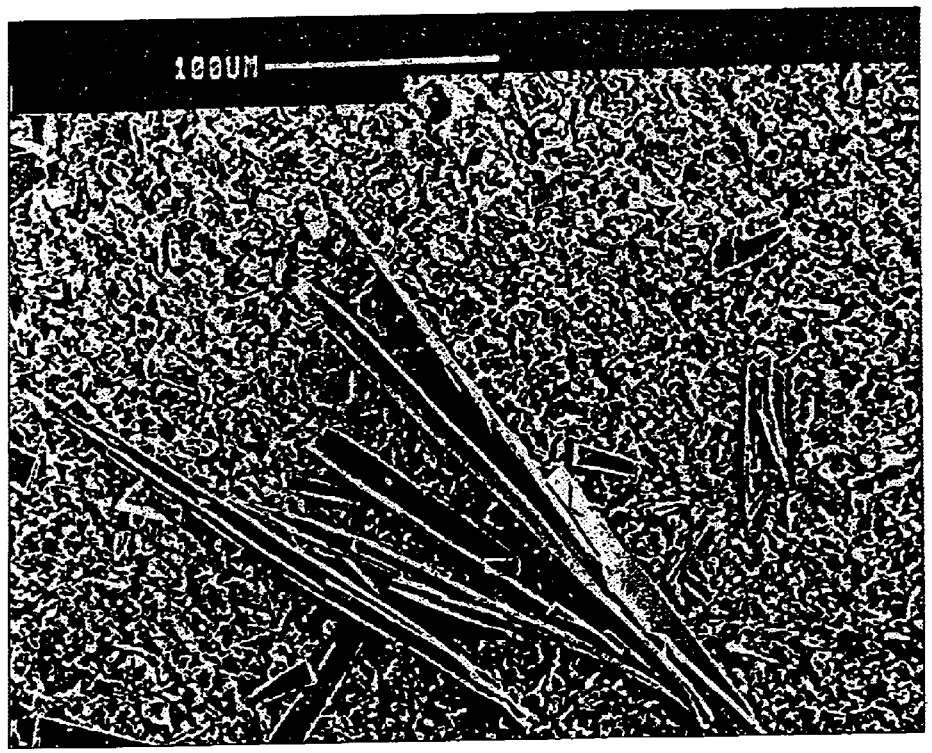

A solution of salmeterol xinafoate in 96% ethanol (0.8 w/v) was co-introduced with $CO_2$ at 300 bar and either 50° C. or 60° C. via a coaxial nozzle into the particle formation vessel using the apparatus described and shown in FIG. 1. The dry, easily handlable products without significant static charge were examined by SEM. The product obtained at 50° C. was composed of blade-like shaped particles with reduced elongation (See FIG. 17) compared with the acicular, needle shaped particles produced at 60° C. (See FIG. 18).

In another experiment, a solution of salmeterol xinafoate in acetone (0.6% w/v) was co-introduced with $CO_2$ at 200 bar and 50° C. via a coaxial nozzle into the particle formation vessel using the apparatus described and shown in FIG. 1.

Figure 19:
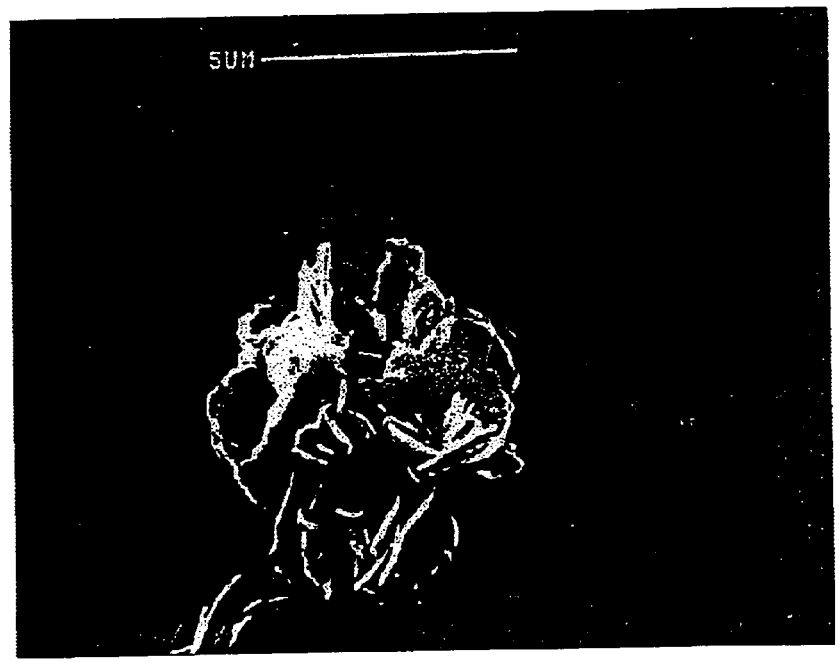

The dry, easily handlable products without significant static charge was examined by SEM (see FIG. 19) and particles were found to be plate-like microcrystalline accretions.

Thus by controlling the working conditions of the particle formation process, salmeterol xinafoate products composed of particles having different particle shapes can be produced.

EXAMPLE 5

Figure 20:
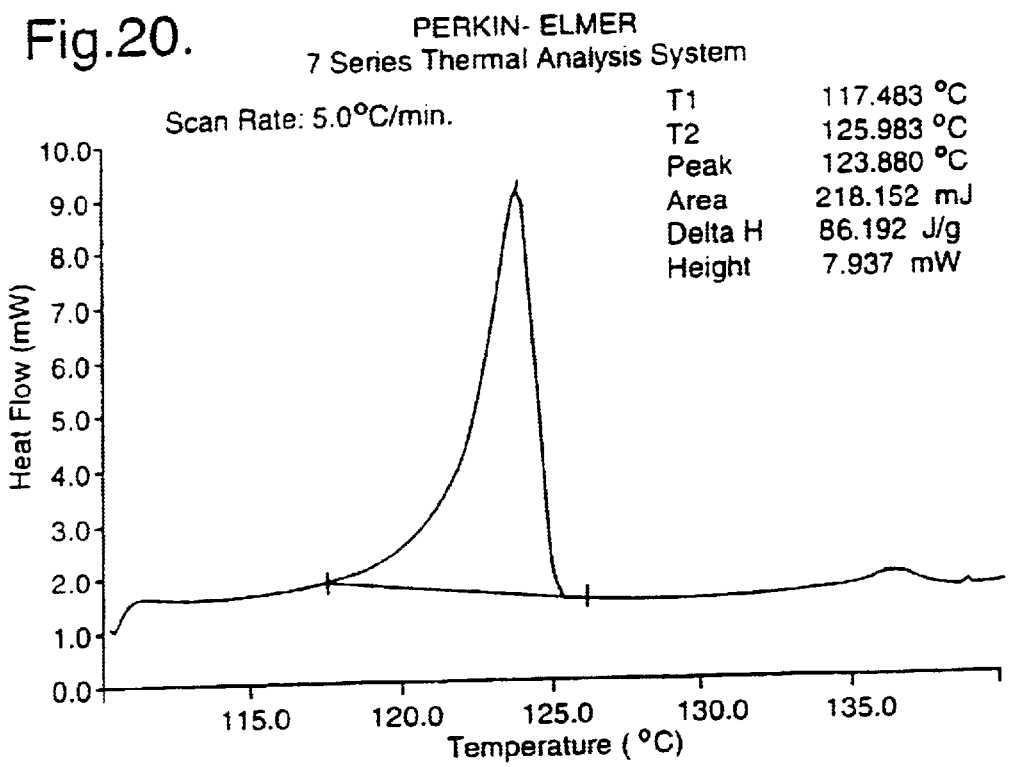
FIG. 20 is a DSC profile of salmeterol xinafoate deposited onto silicon dioxide fumed particles, as prepared in Example 5.
Figure 21:
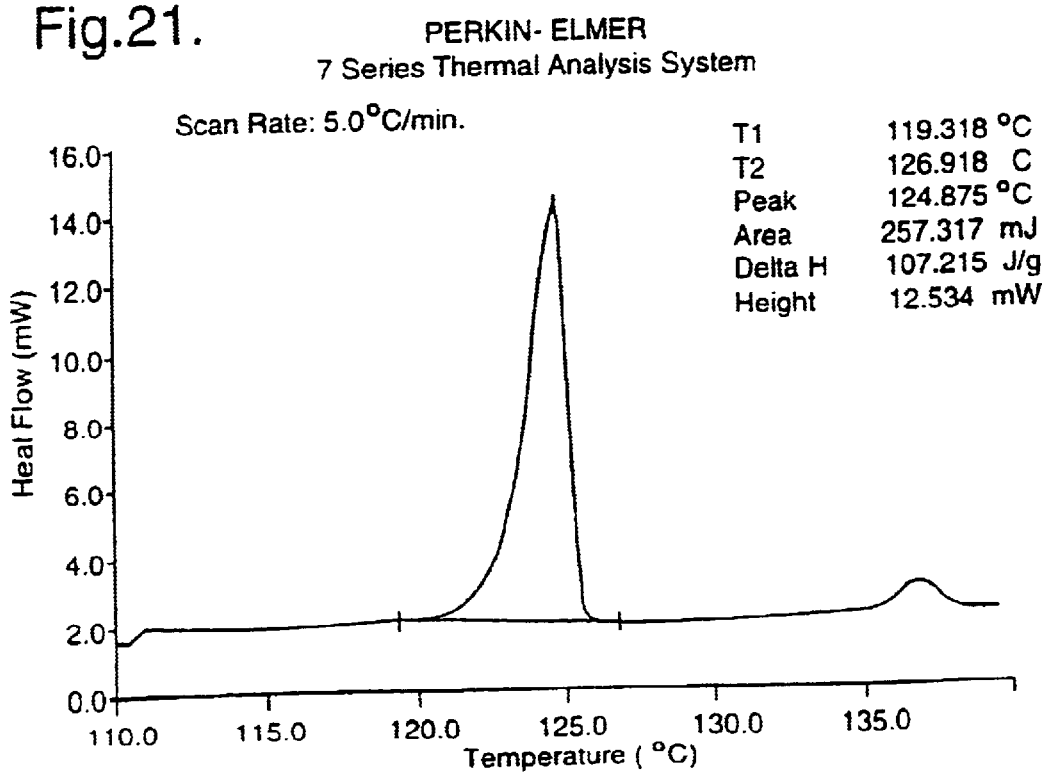
FIG. 21 is a DSC profile of salmeterol xinafoate, as prepared in Example 5 for comparison.
Figure 22:
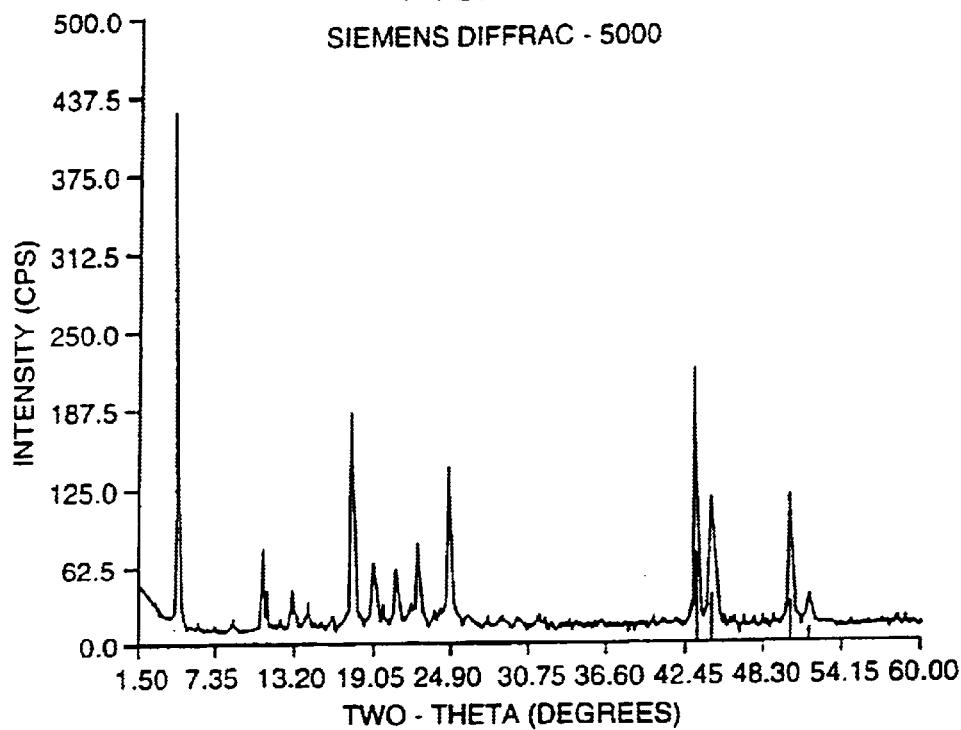
FIG. 22 is an XRD pattern of salmeterol xinafoate deposited onto silicon dioxide fumed particles, as prepared in Example 5.
Figure 23:
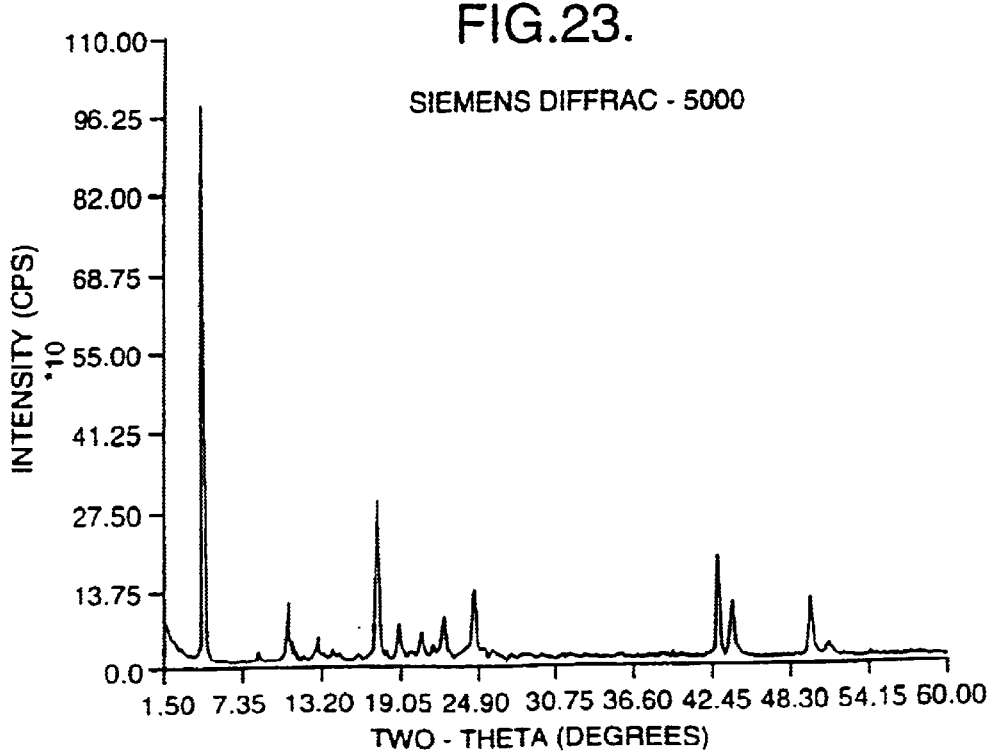
FIG. 23 is an XRD pattern of salmeterol xinafoate, as prepared in Example 5 for comparison.

Formation of Particles with Salmeterol Xinafoate Deposited onto a Solid Substrate A solution of salmeterol xinafoate in methanol (0.6% w/v) also containing a dispersion of silicon dioxide fumed B.P. (0.06% w/v) was co-introduced with $CO_2$ at 300 bar and 45° C. via a coaxial nozzle into the particle formation vessel using the apparatus described and shown in FIG. 1. A second methanol solution, as above, but without dispersed silicon dioxide fumed B.P. was similarly co-introduced, into the particle formation vessel under equivalent working conditions. The resultant dry, easily handlable powdered products without significant static charge were examined by differential scanning calorimetry (DSC) (see FIGS. 20 and 21) and X-ray power diffraction (XRD) (see FIGS. 22 and 23). The DSC profile for the sample with salmeterol xinafoate deposited onto the silicon dioxide fumed particles (FIG. 20) showed a wider melting endotherm with a lower peak heat flow temperature than that for the salmeterol xinafoate sample without silicon dioxide fumed prepared under equivalent conditions (FIG. 21). The XRD pattern for the sample with salmeterol xinafoate deposited onto the silicon dioxide fumed particles (FIG. 22) exhibited reduced crystallinity as indicated by the reduction in measured intensity valves than that for the salmeterol xinafoate sample without silicon dioxide fumed prepared under equivalent conditions (FIG. 23).

These data indicate the deposition of salmeterol xinafoate onto the silicon dioxide fumed particle substrates with changes in the degree of crystallinity of salmeterol xinafoate, compared with samples of salmeterol xinafoate prepared under equivalent working conditions without silicon dioxide fumed particles as a solid substrate.

EXAMPLE 6

Use of Larger Scale Apparatus

FIGS. 26 and 27A–F show the construction of a relatively large-scale particle formation vessel 90 which may be used in apparatus as described herein. The vessel includes an inner reaction chamber 91 and vessel wall 92 and a screw-threaded end cap 93 engageable with the upper end of wall 92. A lid 93 has a central opening 95 for a nozzle assembly and a peripheral opening 96 for an outlet, which will contain a particle retaining device (e.g. a filter).

In the FIGS. 27, A–C show the main vessel with its vessel wall 92; D shows the end cap 93; E shows the lid 93 and F an O-ring seal 97 used to seal the upper end of the reaction chamber 91. Dimensions in mm are shown for the various components.

Vessel 90 was used with a two-passage nozzle to produce salmeterol xinafoate. Operating conditions were a 1.25% w/v solution of salmeterol xinafoate in acetone, at 100 bar and 60° C. An X-ray powder diffraction pattern (FIG. 28) is provided for the sample obtained.

Clearly, the process described herein may be carried out using relatively large-scale apparatus and still be effective in the controlled formation of particle products.

EXAMPLE 7

Effect of Operating Conditions on Particle Size

The process was carried out in a similar manner to that described in Examples 1–5, using a particle formation vessel of 50 ml capacity and a two-passage nozzle, in order to produce particles of salmeterol xinafoate. The effects of changing temperature, pressure and supercritical fluid flow rate, on the mean size of the product particles, were investigated. The results are shown in FIGS. 29–31.

FIG. 29 is a graph of mean particle size diameter (microns), measured using the Malvern sizing technique, versus temperature (°C.) in the particle formation vessel. The salmeterol xinafoate was precipitated at 300 bar from acetone. The quoted flow rates represent acetone/salmeterol solution flow rates at a constant $CO_2$ flow of 9 ml/min.

FIG. 30 shows the effect of vessel pressure on particle size at four different temperatures. Flow rates were 0.1 ml/min for the acetone solution and 9 ml/min for the $CO_2$.

FIG. 31 shows a graph of $CO_2$ ("SF") flow rate versus particle size, the salmeterol xinafoate being precipitated from acetone at an acetone/salmeterol solution flow rate of 0.3 ml/min and a 1.25% w/v concentration. The operating temperature was 60° C., the pressure 120 bar.

EXAMPLE 8

Use of Three-Passage Nozzle

Figure 2A:
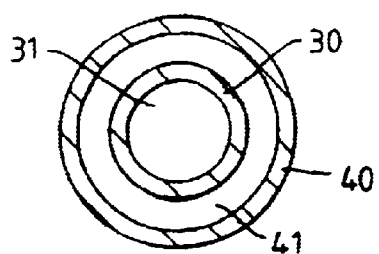
FIG. 2A shows a cross-section of a coaxial nozzle for use in the apparatus described herein.
Figure 2B:
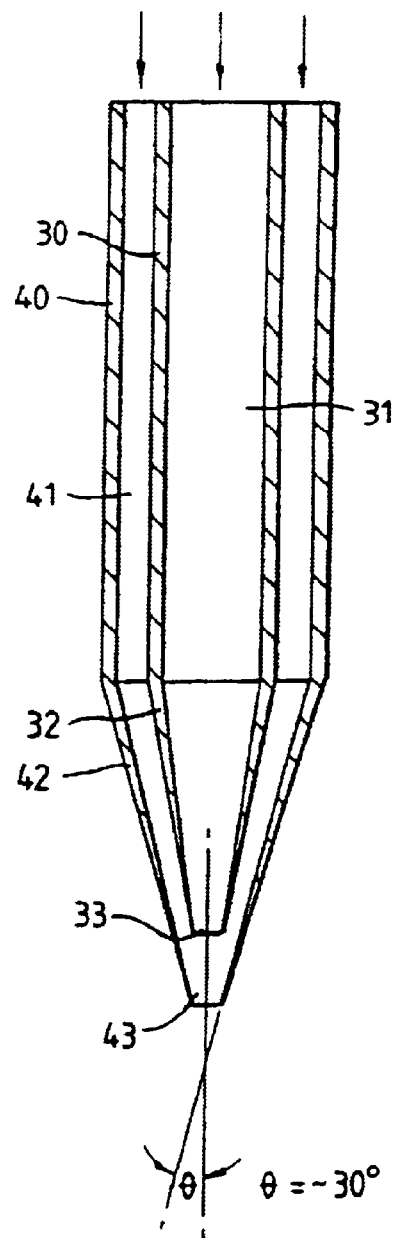
FIG. 2B shows a longitudinal section of the tip of a coaxial nozzle for use in the apparatus described herein.
Figure 3:
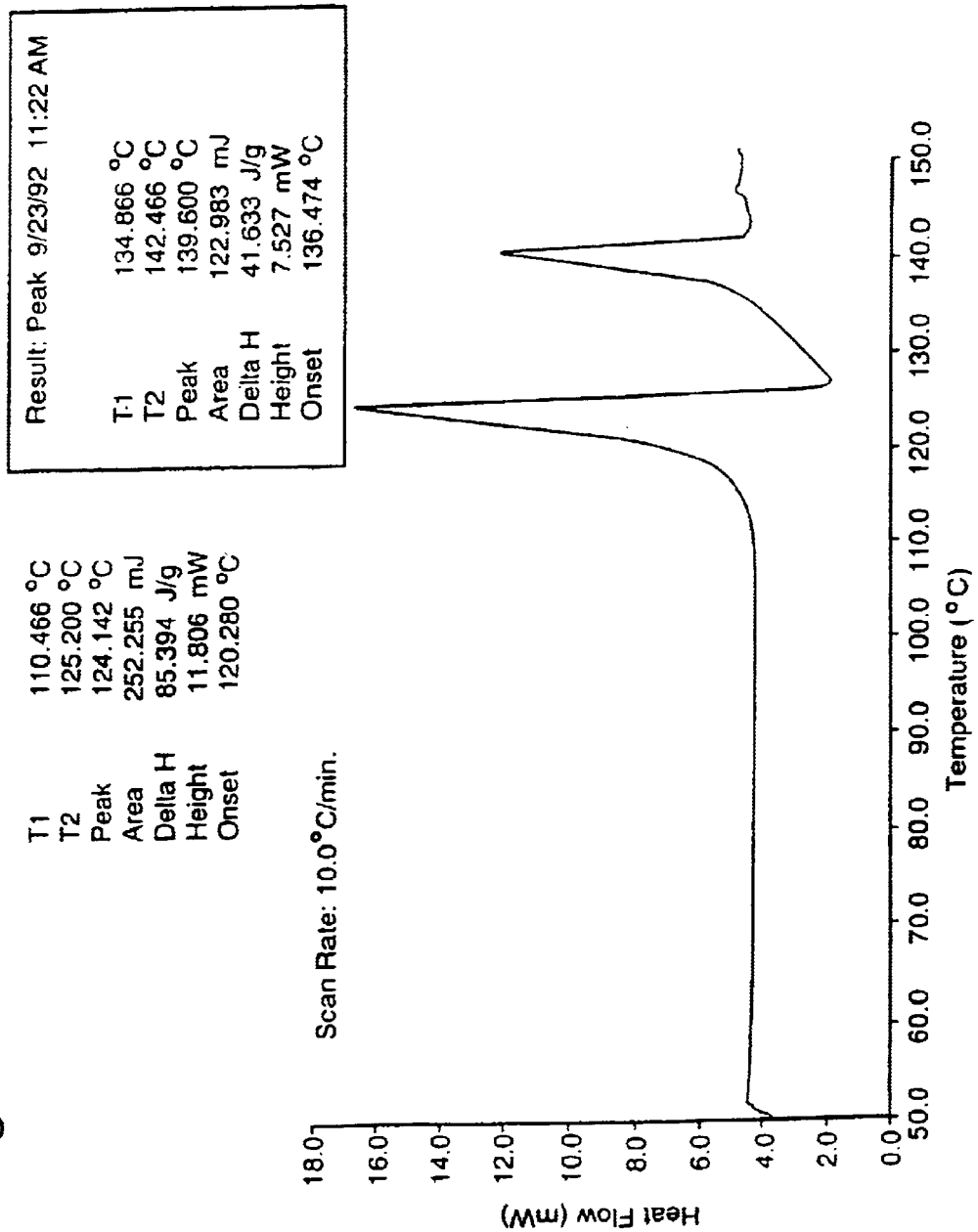
FIG. 3 is a differential scanning calorimetry (DSC) profile of conventionally crystallised salmeterol xinafoate.

The above examples were all carried out using apparatus similar to that shown in FIG. 1, and a two-passage inlet nozzle of the type shown in FIGS. 2A and 2B. In contrast, the present example was carried out using a three-passage inlet nozzle of the type shown in FIG. 25, having the following dimensions:

|  | External diameter | Internal diameter |
|---|---|---|
| Outer tube 70 | 1.54 mm | 0.75 mm |
| Intermediate tube 60 | 0.70 mm | 0.35 mm |
| Inner tube 50 | 0.30 mm | 0.15 mm |

Nozzle opening: 0.22 mm internal diameter.

All tubes of the nozzle were made of stainless steel. The particle formation vessel used had a capacity of 32 ml.

A sample of salmeterol xinafoate was prepared from a 0.5% w/v acetone solution at 200 bar and 50° C., using an acetone/salmeterol solution flow rate of 0.2 ml/min through the intermediate nozzle passage, and a $CO_2$ flow rate through the inner and outer nozzle passages of 5 ml/min. FIG. 32 shows X-ray data for the sample obtained.

EXAMPLE 9

Reduced Static Charge—Salmeterol Xinafoate

Using samples prepared as described in Example 1, a simple test was devised to determine their relative static charge based on the quantity of drug remaining coated to the walls of a vial after rolling a predetermined quantity of drug in the vial for 5 minutes. The greater the drug remaining on the vial, the higher the relative static charge associated with the drug substance. Results are shown in Table 4.

TABLE 4

| Sample | % Drug Retaining on Vial |
|---|---|
| Conventionally crystallised salmeterol xinafoate (micronised) | 7.0 |
| SCF Salmeterol xinafoate, sample 1 | 2.5 |
| SCF Salmeterol xinafoate, sample 2 | 5.7 |

The results indicate a lower relative static charge for the SCF salmeterol xinafoate compared to conventionally crystallised salmeterol xinafoate (micronised). In contrast to conventionally crystallised salmeterol xinafoate, the SCF salmeterol xinafoate has no significant static charge when first formed. The lower relative static charge has several advantages; improved flow properties, improved fluidisability and better drug deposition in the lungs from dry powder formulations.

EXAMPLE 10

Preparation of a Salmeterol Xinafoate and Polymer Matrix

An acetone solution containing 0.45% w/v of salmeterol xinafoate and 0.05% w/v hydroxypropylcellulose (Klucel SL) was prepared and fed into apparatus similar to that shown in FIG. 1, using a two-passage nozzle and a 50 ml particle formation vessel. The operating conditions were 120 bar and 60° C., with flow rates of 0.4 ml/min for the salmeterol/polymer solution and 9 ml/min for the supercritical $CO_2$. A fine, white powder containing 10% w/v hydroxypropylcellulose in salmeterol xinafoate was obtained as a product.

A product of similar appearance, but containing 20% w/v hydroxypropylcellulose, was also prepared from a second solution, using the same operating conditions as for the first product.

FIGS. 33 and 34 are X-ray powder diffractogram profiles for the first and second samples respectively. Increasing disturbance of the crystalline salmeterol xinafoate can be seen with increasing hydroxypropylcellulose content, confirming the inclusion of the polymer matrix material into the sample.

This example thus illustrates how the process described may be used to prepare multi-component particles containing salmeterol xinafoate in a polymer matrix. The incorporated second component may be a pharmaceutically acceptable carrier such as a polymer (e.g. starch or hydroxypropylcellulose), silicon dioxide, sorbitol, mannitol or lactose. It may be used to modify the dissolution performance or other properties of a drug.

EXAMPLE 11

Reproducibility

Two different solutions of salmeterol xinafoate in acetone (0.6% w/v) were made and each solution was co-introduced with $CO_2$ via a coaxial nozzle into the particle formation vessel using the apparatus described on two different days to give samples A and B. The operating conditions were 300 bar and 35° C., with flow rates of 0.2 ml/min for the salmeterol solution and 6 ml/min for the supercritical $CO_2$. The crystallised salmeterol xinafoate provided from each solution was examined for particle size and size distribution.
a) Particle Size and Distribution The particle size and distribution was determined by laser diffraction (Malvern Mastersizer), see Table 5.

TABLE 5

|  | Mean Particle Size (Microns) | % < 5 microns | % < 10 microns | Uniformity Index |
|---|---|---|---|---|
| Sample A | 7.2 | 31.6 | 67.8 | 9 |
| Sample B | 7.7 | 28.3 | 64.5 | 9 |

The results from the particle size analysis show that the process is essentially reproducible when using the same crystallising parameters.

EXAMPLE 12

Enhancement of Purity of a Particulate Product

This example shows how the method described herein may be used to enhance the purity of the particulate product, on precipitation of the product from a solution containing impurities.

0.2022 g of salmeterol xinafoate was mixed with 0.0242 g of salicylic acid, analar grade (BDH Chemicals Ltd, UK) (the "impurity"), dissolved in 60 ml of absolute ethanol and fed to a 50 ml particle formation vessel through a two-passage nozzle. The operating conditions were 200 bar and 50° C.; a solution (10.69% w/v salicylic acid in salmeterol) flow rate of 0.3 ml/min; and a supercritical $CO_2$ flow rate of 9 ml/min.

The product, a white fluffy powder, was collected and analysed using HPLC.

The analysis was carried out, utilising a Pye Unicam PU4015 HPLC system (Pye Unicam Ltd, UK), and a column 150×4.6 mm packed with 5 micron Spherisorb ODS2 (Jones Chromatography, UK). The mobile phase consisted of acetonitrile, 0.1 M aqueous ammonium acetate and 0.1 M aqueous sodium dodecyl sulphate (52:24:24 v/v) and the pH was adjusted to 3.8 with glacial acetic acid. The flow rate of the mobile phase was 2.0 ml/min. The injection volume of the sample solutions prepared (5 mg/ml±0.5 mg concentration) was 20 µl and the UV detector was set at 278 nm and the integrator (Hewlett Packard HP3394A) at an attenuation of 8.

FIG. 35 is an HPLC chromatogram for the pure salmeterol xinafoate used in the experiment. FIG. 36 is an HPLC chromatogram for the pure salicylic acid used. FIG. 37 is an HPLC chromatogram for the salmeterol/salicylic acid solution fed into the particle formation vessel, and FIG. 42 an HPLC chromatogram for the product obtained through carrying out the SCF method described herein.

FIGS. 37 and 38 reveal a significant improvement in the purity of the salmeterol xinafoate and an important reduction in the salicylic acid concentration from 10.69% w/v to less than 0.8% w/v. This confirms the ability of the technique described herein to extract, selectively, one or more impurities from a sample and hence to enhance the purity of a desired particulate product.

EXAMPLE 13

Preparation of a Salmeterol Xinafoate and Polymer Matrix (Alternative Method)

A similar experiment to Example 10 was carried out, but using a three-passage nozzle to co-introduce separate solutions of the salmeterol xinafoate and hydroxypropylcellulose, so as to allow mixing of the two components immediately prior to particle formation.

Two separate solutions in acetone were prepared: hydroxypropylcellulose (Klucel SL) at 0.05% w/v and salmeterol xinafoate at 0.45% w/v. These were co-introduced with supercritical $CO_2$ into a 32 ml particle formation vessel. The working conditions were 120 bar and 60° C. The flow rates were 9 ml/min for the $CO_2$ (inner nozzle passage); 0.2 ml/min for the polymer solution (intermediate passage); and 0.2 ml/min for the salmeterol solution (outer passage).

This use of the three-passage nozzle allows the two reactants (drug and polymer) to be rapidly mixed in situ prior to their dispersion by the supercritical fluid.

A white fluffy powder was obtained as a product. A product of similar appearance was obtained using a 0.1% w/v solution of hydroxypropylcellulose and a 0.4% w/v solution of salmeterol xinafoate. FIGS. 39 and 40 are XRD patterns for the first and second products respectively. Increasing disturbance of the crystalline salmeterol xinafoate can be seen with increasing polymer content, confirming the inclusion of the polymer matrix material into the product.

The XRD patterns are comparable to those obtained in Example 10. This supports the belief that rapid mixing of the two materials takes place in situ, before dispersion by the supercritical fluid, when using the three-passage nozzle in this way.

EXAMPLES 14 AND 15

Performance of Metered Dose Inhalers

Metered dose inhalers (MDIs) were manufactured, containing salmeterol xinafoate and propellant, and used in the following tests. The inhalers were 25 microgram, 120 actuation models.

The inhalers were prepared by dispensing 6.4 mg drug (prepared according to Example 1 or conventionally micronised) into an 8 ml Presspart aluminium can. The can was closed by crimping on a Valois DF60 63 microlitre Valve before pressure-filling the canister with 12 g of Propellant HFA134a.

The performance of the MDIs was measured based on drug deposition on the valve and actuator; and dose delivered through use.

EXAMPLE 14a

Drug Deposition

Valve

The drug deposited on the valve was measured at the end of use of the inhaler (after actuations 119 & 120). After the appropriate number of actuations, the inhaler exterior was washed in methanol to remove any residual drug deposited on the surface. The inhaler was then cooled in dry ice, the valve removed and the valve components in contact with the suspension (exterior) were washed into a volumetric flask with 50 ml methanol. The valve was disassembled and the valve components in contact with the metered dose (interior) washed into a volumetric flask with 50 ml methanol. The resultant solutions were assayed by HPLC. Table 1 presents the valve drug deposition for Salmeterol Xinafoate/HFA134a inhalers, 25 microgram, 120 actuation.

TABLE 1

The Metered Dose Inhaler Drug Deposition of Salmeterol Xinafoate/HFA134a Inhaler, 25 microgram, 120 actuation

| Drug | Conventionally crystallised salmeterol xinafoate (micronised) | Salmeterol xinafoate of the present invention (sample a) | Salmeterol xinafoate of the present invention (sample b) |
|---|---|---|---|
| Total Valve Drug Deposition (mg) | 0.34 | 0.13 | 0.15 |
| Interior Valve Drug Deposition (mg) | 0.12 | 0.05 | 0.05 |
| Exterior Valve Drug Deposition (mg) | 0.22 | 0.08 | 0.10 |

Salmeterol xinafoate formulations of the present invention show significantly lower drug deposition on the valve than formulations employing conventionally produced salmeterol xinafoate. As a result of the lower drug deposition, the concentration of drug in the suspension is higher, leading to higher quantities of drug being delivered from the inhaler.

EXAMPLE 14a

Drug Deposition

Actuator

The drug deposited on the actuator was measured at the beginning of use of the inhaler (after actuations 1 to 10). After the appropriate number of actuations, the inhaler was removed from the actuator and the drug found on the actuator washed into a volumetric flask with 100 ml methanol. The resultant solutions were assayed by HPLC. Table 2 presents the actuator drug deposition and delivered dose for Salmeterol Xinafoate/HFA134a inhalers, 25 microgram, 120 actuation.

TABLE 2

The Metered Dose Inhaler Drug Deposition of Salmeterol Xinafoate/HFA134a Inhaler, 25 microgram, 120 actuation.

| Drug | Conventionally crystallised salmeterol xinafoate (micronised) | Salmeterol xinafoate of the present invention (sample a) | Salmeterol xinafoate of the present invention (sample b) |
|---|---|---|---|
| Actuator Drug Deposition (mcg per actuation) | 3.2 | 2.4 | 2.8 |
| Actuator Drug Deposition (% of total dose) | 14.1 | 10.6 | 11.4 |
| Delivered Dose (mcg per actuation) | 19.6 | 20.2 | 21.7 |
| Total Dose (mcg per actuation) | 22.8 | 22.6 | 24.5 |

Salmeterol xinafoate formulations of the present invention show lower drug deposition on the actuator than formulations employing conventionally produced salmeterol xinafoate. As a result of the lower drug deposition, there is a higher quantity of drug in the delivered dose from the inhaler.

EXAMPLE 15

Dose Delivered Through Use

Doses were collected as pairs of actuations at the beginning of use (actuations 1 & 2) and the end of use (actuations 119 & 120). The doses were collected as follows: The two actuations were fired into a 500 ml separating funnel (plugged at one end with cotton wool) which has a 20 liter per minute airflow pulled through it. The separating funnel was washed with methanol into a 100 ml volumetric flask. The resultant solution is made up to volume and assayed by HPLC.

Table 3 and FIG. 1 presents the Dose Delivered through use data of Salmeterol xinafoate/HFA134a Inhaler, 50 microgram, 120 actuation for which the target dose delivered is 21 microgram.

TABLE 3

The Dose Delivered through use of Salmeterol Xinafoate/HFA134a Inhaler, 25 microgram, 120 actuation.

| Drug | Beginning of use (Actuation 1 & 2) | | End of use (Actuation 119 & 120) | | Overall Mean | | Number of data points outside ± 15% |
|---|---|---|---|---|---|---|---|
| | Mean (mcg) | RSD (%) | Mean (mcg) | RSD (%) | Mean (mcg) | RSD (%) | of Overall mean dose |
| Conventionally crystallised Salmeterol xinafoate (micronised) | 19.3 | 5.1 | 25.5 | 5.5 | 22.4 | 15.1 | 7 |
| Salmeterol xinafoate of the present invention (sample a) | 21.2 | 6.9 | 25.6 | 5.6 | 23.5 | 11.2 | 3 |
| Salmeterol xinafoate of the present invention (sample b) | 20.8 | 2.7 | 26.3 | 5.6 | 23.5 | 12.9 | 1 |

Salmeterol xinafoate formulations of the present invention show a flatter dosing profile through the life of the inhaler. This profile is better than that of conventionally crystallised salmeterol xinafoate formulations (micronised) which show a larger increase in dose per actuation through use of the inhaler.

The dose variability at each point through the use of the inhaler for salmeterol xinafoate formulations of the present invention is comparable with that of conventionally crystallised drug (micronised). But, the overall variability is lower, which is also indicated by fewer data points outside ±15% of the overall mean dose, for salmeterol xinafoate inhaler formulations of the present invention due to the flatter dosing profile.

The delivered dose for salmeterol xinafoate formulations of the present invention is consistently higher than that of conventionally crystallised salmeterol xinafoate formulations (micronised), due to the lower drug deposition on the actuator and valve as discussed in Example 14.

What is claimed is:

1. An aerosol pharmaceutical formulation comprising salmeterol xinafoate with a controlled particle size, shape and morphology and which has a dynamic bulk density in the range of between 0.01 and 0.1 g.cm$^{-3}$, and a fluorocarbon, hydrogen-containing fluorocarbon or hydrogen-containing chlorofluorocarbon propellant.

2. An aerosol pharmaceutical formulation comprising salmeterol xinafoate as prepared by supercritical fluid particle formation/and a fluorocarbon, hydrogen-containing fluorocarbon or hydrogen-containing chlorofluorocarbon propellant.

3. An aerosol pharmaceutical formulation comprising salmeterol xinafoate in a form with a dynamic bulk density of less than 0.1 g.cm$^{-3}$ and a fluorocarbon, hydrogen-containing fluorocarbon or hydrogen-containing chlorofluorocarbon propellant.

4. An aerosol pharmaceutical formulation according to claim 1 in which the salmeterol xinafoate has a dynamic bulk density in the range between 0.01 and 0.1 g.cm-3.

5. An aerosol pharmaceutical formulation according to claim 1 in which the salmeterol xinafoate has a dynamic bulk density in the range between 0.01 and 0.075 g.cm$^{-3}$.

6. An aerosol pharmaceutical formulation according to claim 1 in which the propellant is 1,1,1,2-tetrafluoroethane.

7. An aerosol pharmaceutical formulation according to claim 6 in which the weight ratio of drug to propellant is between 0.025:75 and 0.1:75.

8. An aerosol pharmaceutical formulation according to claim 6 in which the weight ratio of drug to propellant is 0.05:75.

9. An aerosol pharmaceutical formulation according to claim 1 in which the salmeterol xinafoate has a particle size in the range 1 to 10 microns.

10. An aerosol pharmaceutical formulation according to claim 9 in which the salmeterol xinafoate has a particle size in the range 1 to 5 microns.

11. An aerosol pharmaceutical formulation according to claim 1 in which the salmeterol xinafoate has a uniform particle size distribution, as measured by a uniformity coefficient of from 1 to 20.

12. An aerosol pharmaceutical formulation according to claim 1 in which the salmeterol xinafoate has a cohesivity of 0 to 20%.

13. An aerosol pharmaceutical formulation comprising substantially pure particulate Polymorph I salmeterol xinafoate having a dynamic bulk density in the range of between 0.01 and 0.1 g.cm$^{-3}$, and a fluorocarbon, hydrogen-containing fluorocarbon or hydrogen-containing chlorofluorocarbon propellant.

14. An aerosol pharmaceutical formulation comprising substantially pure particulate Polymorph II salmeterol xinafoate having a dynamic bulk density in the range of between 0.01 and 0.1 g.cm$^{-3}$, and a fluorocarbon, hydrogen-containing fluorocarbon or hydrogen-containing chlorofluorocarbon propellant.

15. An aerosol pharmaceutical formulation comprising multicomponent particles of salmeterol xinafoate and a pharmaceutically acceptable carrier with a controlled particle size, shape and morphology, and having a dynamic bulk density in the range of between 0.01 and 0.1 g.cm$^{-3}$, and a fluorocarbon, hydrogen-containing fluorocarbon or hydrogen-containing chlorofluorocarbon propellant.

16. An aerosol pharmaceutical formulation according to claim 1 further comprising one more additional particulate medicaments.

17. An aerosol pharmaceutical formulation according to claim 16 wherein the additional medicament is selected from the group consisting of sodium cromoglycate, fluticasone propionate and beclomethasone dipropionate.

18. An aerosol pharmaceutical formulation according to claim 1 which contains 0.03–0.13% w/v of salmeterol xinafoate and optionally one or more additional medicaments relative to the total weight of the formulation.

19. An aerosol pharmaceutical formulation according to claim 1 which contains 0.07% w/v of salmeterol xinafoate and optionally one or more additional medicaments relative to the total weight of the formulation.

20. An aerosol pharmaceutical formulation consisting essentially of salmeterol xinafoate with a controlled particle size, shape and morphology, and having a dynamic bulk density in the range of between 0.01 and 0.1 $g.cm^{-3}$, and one or more fluorocarbon, hydrogen-containing fluorocarbon or hydrogen-containing chlorofluorocarbon propellants.

21. A metered dose inhaler containing an aerosol pharmaceutical formulation according to claim 1.

22. A filled canister for a metered dose inhaler containing an aerosol pharmaceutical formulation according to claim 1.

23. A method of treating respiratory disorders which comprises administration by inhalation of an effective amount of a formulation according to claim 1.

24. A method of treating a respiratory disorder which is asthma which comprises administration by inhalation of an effective amount of a formulation according to claim 1.

25. An aerosol formulation according to claim 13 which additionally contains fluticasone propionate.

26. An aerosol formulation according to claim 14 which additionally contains fluticasone propionate.

* * * * *